United States Patent
Flohr et al.

(10) Patent No.: US 9,540,384 B2
(45) Date of Patent: Jan. 10, 2017

(54) PYRROLIDINO HETEROCYCLES

(71) Applicant: Hoffmann-La Roche Inc., Little Falls, NJ (US)

(72) Inventors: Alexander Flohr, Loerrach (DE); Katrin Groebke Zbinden, Liestal (CH); Matthias Koerner, Grenzach-Wyhlen (DE); Christian Lerner, Binningen (CH)

(73) Assignee: Hoffmann-La Roche, Inc., Little Falls, NJ (US)

( * ) Notice: Subject to any disclaimer, the term of this patent is extended or adjusted under 35 U.S.C. 154(b) by 0 days.

(21) Appl. No.: 14/554,484

(22) Filed: Nov. 26, 2014

(65) Prior Publication Data

US 2015/0087644 A1     Mar. 26, 2015

Related U.S. Application Data

(63) Continuation of application No. PCT/EP2013/060833, filed on May 27, 2013.

(30) Foreign Application Priority Data

May 30, 2012  (EP) .................... 12169958

(51) Int. Cl.
| | |
|---|---|
| *C07D 487/04* | (2006.01) |
| *C07D 213/68* | (2006.01) |
| *C07D 401/06* | (2006.01) |
| *C07D 401/12* | (2006.01) |
| *C07D 401/14* | (2006.01) |
| *A61K 31/4427* | (2006.01) |
| *A61K 31/4439* | (2006.01) |
| *A61K 31/444* | (2006.01) |
| *C07D 405/14* | (2006.01) |
| *C07D 213/74* | (2006.01) |
| *C07D 413/06* | (2006.01) |
| *C07D 473/30* | (2006.01) |

(52) U.S. Cl.
CPC ........... *C07D 487/04* (2013.01); *C07D 213/68* (2013.01); *C07D 213/74* (2013.01); *C07D 401/06* (2013.01); *C07D 401/12* (2013.01); *C07D 401/14* (2013.01); *C07D 405/14* (2013.01); *C07D 413/06* (2013.01); *C07D 473/30* (2013.01)

(58) Field of Classification Search
CPC .............. C07D 295/023; C07D 265/30; C07D 295/027; C07D 213/74; C07C 213/02
USPC ....... 544/106, 116, 263, 264, 265, 277, 281, 544/287, 350; 514/234.2, 250, 259.2, 514/259.3, 259.31, 263.1, 263.4, 263.3, 514/266.3; 546/256
See application file for complete search history.

(56) References Cited

FOREIGN PATENT DOCUMENTS

| WO | 01/44250 A1 | 6/2001 |
|---|---|---|
| WO | WO 2004064721 A2 * | 8/2004 |
| WO | 2010/030027 A1 | 3/2010 |
| WO | WO 2010060854 A1 * | 6/2010 |
| WO | 2011/076723 A1 | 6/2011 |
| WO | 2011/150156 A2 | 12/2011 |
| WO | 2011/150156 A3 | 12/2011 |
| WO | 2012/054366 A2 | 4/2012 |
| WO | 2012/054366 A3 | 4/2012 |

OTHER PUBLICATIONS

Bolliger, J., M. Oberholzer, and C. Frech "Access to 2-Aminopyridines—Compounds of Great Biological and Chemical Significance" Adv. Synth. Catal. (2011), 353: pp. 945-954.*
International Search Report and Written Opinion for International Patent application No. PCT/EP2013/060833.

* cited by examiner

*Primary Examiner* — Alicia L Otton
*Assistant Examiner* — Sagar Patel

(57) ABSTRACT

The invention relates to compounds of formula I

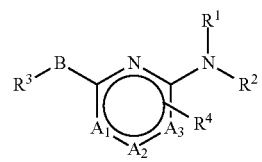

wherein $A_1$, $A_2$, $A_3$, B, $R^1$, $R^2$, $R^3$ and $R^4$ are as defined in the description and in the claims, as well as physiologically acceptable salts thereof. These compounds inhibit PDE10A and can be used as medicaments.

6 Claims, No Drawings

PYRROLIDINO HETEROCYCLES

PRIORITY OF INVENTION

This application claims priority under 35 U.S.C. 120 and 35 U.S.C. 365(c) to International Application Nos. PCT/EP2013/060833 filed on May 27, 2013 and claims priority to 35 U.S.C. 119(a), to European Patent Application No. 12169958.1 filed on May 30, 2012. The entire content of the applications referenced above are hereby incorporated by reference herein.

BACKGROUND OF INVENTION

Schizophrenia is a progressive and devastating neurological disease characterized by episodic positive symptoms such as delusions, hallucinations, thought disorders and psychosis and persistent negative symptoms such as flattened affect, impaired attention and social withdrawal, and cognitive impairments (Lewis D A and Lieberman J A, Neuron, 28:325-33, 2000). For decades research has focused on the "dopaminergic hyperactivity" hypothesis which has led to therapeutic interventions involving blockade of the dopaminergic system (Vandenberg R J and Aubrey K R., Exp. Opin. Ther. Targets, 5(4): 507-518, 2001; Nakazato A and Okuyama S, et al., Exp. Opin. Ther. Patents, 10(1): 75-98, 2000). This pharmacological approach, besides ameliorating positive symptoms in schizophrenic patients, poorly addresses negative and cognitive symptoms which are the best predictors of functional outcome (Sharma T., Br. J. Psychiatry, 174 (suppl. 28): 44-51, 1999). In addition, current antipsychotic treatment is associated with adverse effects like weight gain, extrapyramidal symptoms or effects on glucose and lipid metabolism, related to their unspecific pharmacology.

In conclusion there is still a need for developing new antipsychotics with improved efficacy and safety profile.

SUMMARY OF INVENTION

The present invention relates to a compound of formula (I)

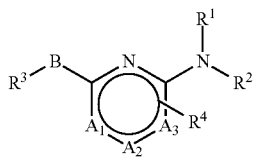

wherein $A_1$, $A_2$ and $A_3$ are independently N or C, with the proviso that $A_1$, $A_2$ and $A_3$ are not simultaneously N, B is $C_1$-$C_4$-alkylene, $C_2$-$C_4$-alkenylene, —O—$C_1$-$C_4$ alkyl or —NH—$C_1$-$C_4$alkyl $R^1$ and $R^2$, are independently selected from hydrogen, $C_1$-$C_7$-alkyl, $C_1$-$C_7$-hydroxyalkyl, $C_3$-$C_8$-cycloalkyl, $R^1$ and $R^2$ together with the nitrogen atom to which they are attached, form a heterocycloalkyl which can be substituted by 1 to 3 substituents independently selected from the group consisting of halogen, $C_1$-$C_7$-alkyl, $C_1$-$C_7$-hydroxyalkyl, $C_1$-$C_7$ alkoxy, $C_1$-$C_7$-haloalkyl, hydroxyl and oxo;

$R^3$ is selected from heteroaryl optionally substituted by 1 to 3 substituents selected from halogen, $C_1$-$C_7$-alkyl, cycloalkyl, $C_1$-$C_7$ alkoxy, $C_1$-$C_7$-haloalkyl, aryl, heteroaryl, —$NR^5R^6$, —O—$R^7$, —C(O)—NR'R'', wherein heteroaryl contains at least one nitrogen atom which is adjacent to the connecting ring carbon atom, $R^4$ is selected from hydrogen, $C_1$-$C_7$-alkyl, $C_3$-$C_8$-cycloalkyl, $R^5$ and $R^6$ are independently selected from hydrogen, $C_1$-$C_7$-alkyl, $R^5$ and $R^6$ together with the nitrogen atom to which they are attached, form a heterocycloalkyl which can be substituted by 1 to 3 substituents independently selected from the group consisting of halogen, $C_1$-$C_7$ alkyl, $C_1$-$C_7$-hydroxyalkyl, $C_1$-$C_7$ alkoxy, $C_1$-$C_7$-haloalkyl and oxo;

$R^7$ is selected from $C_1$-$C_7$-alkyl, $C_1$-$C_7$-haloalkyl and heterocycloalkyl, R' and R'' are independently selected from hydrogen and $C_1$-$C_7$-alkyl.

or a pharmaceutically acceptable salt thereof.

Further, the invention is concerned with a process for the manufacture of the above compounds, pharmaceutical preparations which contain such compounds, the use of these compounds for the production of pharmaceutical preparations and the use of these compounds in the treatment of diseases.

DETAILED DESCRIPTION OF THE INVENTION

A complementary model of schizophrenia was proposed in the mid-1960' based upon the psychotomimetic action caused by the blockade of the glutamate system by compounds like phencyclidine (PCP) and related agents (ketamine) which are non-competitive NMDA receptor antagonists. Interestingly, in healthy volunteers PCP-induced psychotomimetic action incorporates positive and negative symptoms as well as cognitive dysfunction, thus closely resembling schizophrenia in patients (Javitt D C et al., Biol. Psychiatry, 45: 668-679, 1999).

Cyclic nucleotides cyclic adenosine monophosphate (cAMP) and cyclic guanosine monophosphate (cGMP) are ubiquitous second messengers responsible for mediating the biological response of a variety of extracellular signals, including neurotransmitters, light and hormones. cAMP and cGMP regulate a variety of intracellular processes particularly in neurons of the central nervous system by activating cAMP- and cGMP-dependent kinases which then phosphorylate proteins involved in the regulation of synaptic transmission, neuronal differentiation and survival.

A crucial mechanism for controlling intracellular cyclic nucleotide levels and therefore cyclic nucleotide signaling is via hydrolysis of the 3',5'-phosphodiester bond by phosphodiesterases. Phosphodiesterases (PDEs) are a family of widely expressed enzymes encoded by 21 different genes in humans, with each gene encoding several splice variants (Beavo, J., Physiol. Rev. 1995, 75, 725-748; Conti, M., Jin, S. L., Prog. Nucleic Acid Res. Mol. Biol. 1999, 63, 1-38; Soderling, S. H., Beavo, J. A., Curr. Opin. Cell Biol. 2000, 12, 174-179, Manallack, D. T. et al. J. Med. Chem. 2005, 48 (10), 3449-3462).

The PDE families differ in their substrate specificity for the cyclic nucleotides, their mechanism of regulation and their sensitivity to inhibitors. Moreover, they are differentially localized in the organism, among the cells of an organ and even within the cells. These differences lead to a differentiated involvement of the PDE families in the various physiological functions.

PDE10A is a dual substrate PDE encoded by a single gene as reported in 1999 by three separate research groups (Fujishige K., et al., Eur J Biochem (1999) 266(3):1118-

1127, Soderling S. H., et al., Proc Natl Acad Sci USA (1999) 96(12):7071-7076, Loughney K., et al., Gene (1999) 234 (1):109-117). PDE10A is unique from other members of the multigene family with respect to amino acid sequence (779 aa), tissue-specific pattern of expression, affinity for cAMP and cGMP and the effect on PDE activity by specific and general inhibitors.

PDE10A has one of the most restricted distribution of any PDE family being primarily expressed in the brain particularly in the nucleus accumbens and the caudate putamen. Additionally thalamus, olfactory bulb, hippocampus and frontal cortex show moderate levels of PDE10A expression. All these brain areas have been suggested to be involved in the pathophysiology of schizophrenia and psychosis, suggesting a central role of PDE10A in this devastating mental illness. Outside the central nervous system PDE10A transcript expression is also observed in peripheral tissues like thyroid gland, pituitary gland, insulin secreting pancreatic cells and testes (Fujishige, K. et al., J. Biol. Chem. 1999, 274, 18438-18445, Sweet, L. (2005) WO 2005/012485). On the other hand expression of PDE10A protein has been observed only in enteric ganglia, in testis and epididymal sperm (Coskran T. M, et al., J. Histochem. Cytochem. 2006, 54 (11), 1205-1213).

In the striatum both mRNA and protein are expressed only in the GABA (γ-aminobutyric acid)-containing medium spiny projection neurons making it an intriguing target for the treatment of diseases of the central nervous system (Fujishige, K. et al., Eur. J. Biochem. 1999, 266, 1118-1127; Seeger, T. F. et al., Brain Res. 2003, 985, 113-126). The striatal medium spiny neurons are the principal input site and first site for information integration in the basal ganglia circuit of the mammalian brain. The basal ganglia are a series of interconnected subcortical nuclei that integrate widespread cortical input with dopaminergic signaling to plan and execute relevant motor and cognitive patterns while suppressing unwanted or irrelevant patterns (Graybiel, A. M. Curr. Biol. 2000, 10, R509-R511 (2000).

Papaverine, a relatively specific PDE10A inhibitor, and PDE10A-knockout mice have been used to explore the physiology of this enzyme and the possible therapeutic utility of PDE10A inhibition. Inhibition of this enzyme pharmacologically or through gene disruption causes a reduction in activity and a reduced response to psychomotor stimulants Inhibition also reduces the conditioned avoidance response, a behavioural response that is predictive of clinical antipsychotic activity (Siuciak, J. A.; et al., Neuropharmacology 2006, 51 (2), 386-396; Siuciak, J. A.; et al., Neuropharmacology 2006, 51 (2), 374-385).

In addition PDE10A inhibition bears the potential to improve the negative and cognitive symptoms associated to schizophrenia. Indeed papaverine have been shown to attenuate the deficits in the extra-dimensional shift learning induced in rats by sub-chronic treatment with PCP, an animal paradigm of NMDA receptor hypofunction (Rodefer, J. S., et al., Eur. J. Neuroscience 2005, 2: 1070-1076). In addition increased social interaction in PDE10A2-deficient mice have been observed (Sano, H. J. Neurochem. 2008, 105, 546-556).

Diseases that can be treated with PDE10A inhibitors include, but are not limited to, diseases thought to be mediated in part by dysfunction of the basal ganglia, of other parts of the central nervous system and of other PDE10A expressing tissues. In particular, diseases can be treated, where inhibition of PDE10A can have therapeutic effects.

These diseases include, but are not limited to, certain psychotic disorders such as schizophrenia, positive, negative and/or cognitive symptoms associated with schizophrenia, delusional disorder or substance-induced psychotic disorder, anxiety disorders such as panic disorder, obsessive-compulsive disorder, acute stress disorder or generalized anxiety disorder, obsessive/compulsive disorders, drug addictions, movement disorders such as Parkinson's disease or restless leg syndrome, cognition deficiency disorders such as Alzheimer's disease or multi-infarct dementia, mood disorders such as depression or bipolar disorders, or neuropsychiatric conditions such as psychosis, attention-deficit/hyperactivity disorder (ADHD) or related attentional disorders.

The compounds of the present invention are also suitable for the treatment of diabetes and related disorders such as obesity by regulating the cAMP signaling system.

PDE10A inhibitors might also be useful in preventing neurons from undergoing apoptosis by raising cAMP and cGMP levels and, thus, might possess anti-inflammatory properties. Neurodegenerative disorders treatable with PDE10A inhibitors include, but are not limited to, as Alzheimer's disease, Huntington's disease, Parkinson's disease, multiple sclerosis, stroke or spinal cord injury.

The growth of cancer cells is inhibited by cAMP and cGMP. Thus by raising cAMP and cGMP, PDE10A inhibitors can also be used for the treatment of different solid tumors and hematological malignancies such as renal cell carcinoma or breast cancer.

DEFINITIONS

Unless otherwise indicated, the following definitions are set forth to illustrate and define the meaning and scope of the various terms used to describe the invention herein.

It must be noted that, as used in the specification and the claims, the singular forms "a", "an" and "the" include plural referents unless the context clearly dictates otherwise.

When indicating the number of substituents, the term "one or more" means from one substituent to the highest possible number of substitution, i.e. replacement of one hydrogen up to replacement of all hydrogens by substituents.

The term "halogen" refers to fluorine, chlorine, bromine and iodine, more speficially fluorine, chlorine and bromine.

The term "alkyl" denotes a monovalent linear or branched saturated hydrocarbon group of 1 to 12 carbon atoms. In particular embodiments, alkyl has 1 to 7 carbon atoms, and in more particular embodiments 1 to 4 carbon atoms. Examples of alkyl include methyl, ethyl, propyl, isopropyl, n-butyl, iso-butyl, sec-butyl, or tert-butyl.

The term "alkylene" denotes a linear saturated divalent hydrocarbon group of 1 to 7 carbon atoms or a divalent branched saturated divalent hydrocarbon group of 3 to 7 carbon atoms. Examples of alkylene groups include methylene, ethylene, propylene, 2-methylpropylene, butylene, 2-ethylbutylene, pentylene, hexylene.

The term "alkenylene" denotes a linear divalent hydrocarbon chain of 2 to 7 carbon atoms or a branched divalent hydrocarbon chain of 3 to 7 carbon atoms with at least one double bond. Exemplary alkenylene include ethenylene, 2,2-dimethylethenylene, propenylene, 2-methylpropenylene, butenylene, and pentenylene.

The term "alkynylene" denotes a linear divalent hydrocarbon chain of 2 to 6 carbon atoms or a branched divalent hydrocarbon chain of 3 to 6 carbon atoms with at least one triple bond. Exemplary alkynylene include ethynylene, 2,2-dimethylethynylene, propynylene, 2-methylpropynylene, butynylene, and pentynylene.

The term "aromatic" denotes the conventional idea of aromaticity as defined in the literature, in particular in IUPAC—Compendium of Chemical Terminology, 2nd, A. D. McNaught & A. Wilkinson (Eds). Blackwell Scientific Publications, Oxford (1997).

The term "cycloalkyl" denotes a monovalent saturated monocyclic or bicyclic hydrocarbon group of 3 to 10 ring carbon atoms. In particular embodiments cycloalkyl denotes a monovalent saturated monocyclic hydrocarbon group of 3 to 8 ring carbon atoms. Bicyclic means consisting of two saturated carbocycles having one or more carbon atoms in common. Particular cycloalkyl groups are monocyclic. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl, or bicyclo[2.2.2]octanyl.

The term "alkoxy" denotes a group of the formula —O—R', wherein R' is an alkyl group. Examples of alkoxy moieties include methoxy, ethoxy, isopropoxy, and tert-butoxy.

The term "haloalkyl" denotes an alkyl group wherein at least one of the hydrogen atoms of the alkyl group has been replaced by same or different halogen atoms, particularly fluoro atoms. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, or trifluoromethyl. The term "perhaloalkyl" denotes an alkyl group where all hydrogen atoms of the alkyl group have been replaced by the same or different halogen atoms.

The term "aryl" denotes a monovalent aromatic carbocyclic mono- or bicyclic ring system comprising 6 to 10 carbon ring atoms. Examples of aryl moieties include phenyl and naphthyl The term "amino" refers to a monovalent group that has a nitrogen atom with two hydrogen atoms (represented by —NH$_2$).

The term "oxo" when referring to substituents on heterocycloalkyl means that an oxygen atom is attached to the heterocycloalkyl ring. Thereby, the "oxo" may either replace two hydrogen atoms on a carbon atom, or it may simply be attached to sulfur, so that the sulfur exists in oxidized form, i.e. bearing one or two oxygens.

The term "heterocycloalkyl" denotes a monovalent saturated or partly unsaturated mono- or bicyclic ring system of 3 to 9 ring atoms, comprising 1, 2, or 3 ring heteroatoms selected from N, O and S, the remaining ring atoms being carbon. In particular embodiments, heterocycloalkyl is a monovalent saturated monocyclic ring system of 4 to 7 ring atoms, comprising 1, 2, or 3 ring heteroatoms selected from N, O and S, the remaining ring atoms being carbon. Examples for monocyclic saturated heterocycloalkyl are aziridinyl, oxiranyl, azetidinyl, oxetanyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydro-oxazolyl, tetrahydro-pyridinyl, or dihydropyranyl.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, or quinoxalinyl.

Compounds of formula (I) can form pharmaceutically acceptable salts. Examples of such pharmaceutically acceptable salts are salts of compounds of formula (I) with physiologically compatible mineral acids, such as hydrochloric acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salts" refers to such salts.

It will be appreciated that the compounds of general formula (I) in this invention may be derivatised at functional groups to provide derivatives which are capable of conversion back to the parent compound in vivo.

Compounds and Processes

The present invention relates to a compound of formula (I)

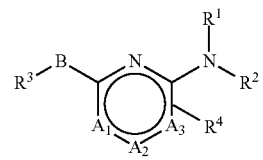

wherein $A_1$, $A_2$ and $A_3$ are independently N or C, with the proviso that $A_1$, $A_2$ and $A_3$ are not simultaneously N, B is $C_1$-$C_4$-alkylene, $C_2$-$C_4$-alkenylene, —O—$C_1$-$C_4$ alkyl or —NH—$C_1$-$C_4$alkyl $R^1$ and $R^2$, are independently selected from hydrogen, $C_1$-$C_7$-alkyl, $C_1$-$C_7$-hydroxyalkyl, $R^1$ and $R^2$ together with the nitrogen atom to which they are attached, form a heterocycloalkyl which can be substituted by 1 to 3 substituents independently selected from the group consisting of halogen, $C_1$-$C_7$-alkyl, $C_1$-$C_7$-hydroxyalkyl, $C_1$-$C_7$ alkoxy, $C_1$-$C_7$-haloalkyl, hydroxyl and oxo;

$R^3$ is selected from heteroaryl optionally substituted by 1 to 3 substituents selected from halogen, $C_1$-$C_7$-alkyl, cycloalkyl, $C_1$-$C_7$ alkoxy, $C_1$-$C_7$-haloalkyl, aryl, heteroaryl, —NR$^5$R$^6$, —O—R$^7$, —C(O)—NH$_2$, wherein heteroaryl contains at least one nitrogen atom which is adjacent to the connecting ring carbon atom, $R^4$ is selected from hydrogen, $C_1$-$C_7$-alkyl, $R^5$ and $R^6$ are independently selected from hydrogen, $C_1$-$C_7$-alkyl, $R^5$ and $R^6$ together with the nitrogen atom to which they are attached, form a heterocycloalkyl which can be substituted by 1 to 3 substituents independently selected from the group consisting of halogen, $C_1$-$C_7$ alkyl, $C_1$-$C_7$-hydroxyalkyl, $C_1$-$C_7$ alkoxy, $C_1$-$C_7$-haloalkyl and oxo;

$R^7$ is selected from $C_1$-$C_7$-alkyl, $C_1$-$C_7$-haloalkyl and heterocycloalkyl.

In a particular embodiment the invention relates to compounds of formula (I), wherein $A_1$, $A_2$ and $A_3$ are independently N or C, with the proviso that $A_1$, $A_2$ and $A_3$ are not simultaneously N, B is $C_1$-$C_4$-alkylene, $C_2$-$C_4$-alkenylene, —O—$C_1$-$C_4$ alkyl or —NH—$C_1$-$C_4$alkyl, $R^1$ and $R^2$, are independently selected from hydrogen, $C_1$-$C_7$-alkyl, $C_1$-$C_7$-hydroxyalkyl, $R^1$ and $R^2$ together with the nitrogen atom to which they are attached, form a heterocycloalkyl which can be substituted by 1 to 3 substituents independently selected from the group consisting of halogen, $C_1$-$C_7$-alkyl, $C_1$-$C_7$-hydroxyalkyl, $C_1$-$C_7$ alkoxy, $C_1$-$C_7$-haloalkyl, hydroxyl and oxo, $R^3$ is selected from heteroaryl optionally substituted by 1 to 3 substituents selected from halogen, $C_1$-$C_7$-alkyl, cycloalkyl, $C_1$-$C_7$ alkoxy, $C_1$-$C_7$-haloalkyl, oxo, aryl, heteroaryl, —$NR^5R^6$, —O—$R^7$, —C(O)—$NH_2$, wherein heteroaryl contains at least one nitrogen atom which is adjacent to the connecting ring carbon atom, $R^4$ is selected from hydrogen, $C_1$-$C_7$-alkyl, $R^5$ and $R^6$ are independently selected from hydrogen, $C_1$-$C_7$-alkyl, $R^5$ and $R^6$ together with the nitrogen atom to which they are attached, form a heterocycloalkyl which can be substituted by 1 to 3 substituents independently selected from the group consisting of halogen, $C_1$-$C_7$ alkyl, $C_1$-$C_7$-hydroxyalkyl, $C_1$-$C_7$ alkoxy, $C_1$-$C_7$-haloalkyl and oxo;

$R^7$ is selected from $C_1$-$C_7$-alkyl, $C_1$-$C_7$-haloalkyl and heterocycloalkyl, with the proviso that the compound of formula (I) excludes the following compounds:

(E)-5,8-Dimethyl-2-(2-(6-(azetidine-1-yl)pyridin-2-yl)vinyl)[1,2,4]triazolo[1,5-a]pyrazine,
5,8-Dimethyl-2-(2-(6-(azetidine-1-yl)pyridin-2-yl)ethyl)-[1,2,4]triazolo[1,5-a]pyrazine,
(E)-5,8-Dimethyl-2-(2-(6-(pyrrolidin-1-yl)pyridin-2-yl)vinyl)[1,2,4]triazolo[1,5-a]pyrazine,
5,8-Dimethyl-2-(2-(6-(pyrrolidin-1-yl)pyridin-2-yl)ethyl)[1,2,4]triazolo[1,5-a]pyrazine,
(E)-5,8-Dimethyl-2-(2-(6-(3-fluoro-pyrrolidin-1-yl)pyridin-2-yl)vinyl)[1,2,4]triazolo[1,5-a]pyrazine,
(E)-5,8-Dimethyl-2-(2-(6-(2-methoxy-pyrrolidin-1-yl)pyridin-2-yl)vinyl)[1,2,4]triazolo[1,5-a]pyrazine,
(E)-5,8-Dimethyl-2-(2-(6-(3-methyl-azetidine-1-yl)pyridin-2-yl)vinyl)[1,2,4]triazolo[1,5-a]pyrazine,
(E)-5,8-Dimethyl-2-(2-(3-methyl-6-(pyrrolidin-1-yl)pyridin-2-yl)vinyl)[1,2,4]triazolo[1,5-a]pyrazine.

In a particular embodiment the invention relates to compounds of formula (I), wherein $A_1$ and $A_2$ and $A_3$ are C.

In a particular embodiment the invention relates to compounds of formula (I), wherein $A_1$ is N and $A_2$ is C.

In a particular embodiment the invention relates to compounds of formula (I), wherein $A_1$ is C and $A_2$ is N.

In a particular embodiment the invention relates to compounds of formula (I), wherein B is $C_2$-$C_4$-alkylene, $C_2$-$C_4$-alkenylene, —O—$C_1$-alkyl, —NH—$C_1$-alkyl, preferably ethylene, ethenylene, —O—$C_1$-alkyl, wherein the O of —O—$C_1$-alkyl is linked to $R^3$.

In a further particular embodiment the invention relates to compounds of formula (I), wherein $R^1$ and $R^2$, together with the nitrogen atom to which they are attached, form a 4 to 6 membered heterocycloalkyl containing one or two heteroatoms selected from N and O, preferably azetidinyl, morpholinyl, pyrrolidinyl, piperidinyl, pyrazolidinyl.

In a further particular embodiment the invention relates to compounds of formula (I), wherein the 4 to 6 membered heterocycloalkyl containing one or two heteroatoms selected from N and O is selected from the group consisting of azetidinyl, morpholinyl, pyrrolidinyl, piperidinyl, pyrazolidinyl, which can be optionally substituted by 1 to 3 substituents selected from the group consisting of $C_1$-$C_7$-alkyl, $C_1$-$C_7$-hydroxyalkyl, hydroxyl and oxo.

In a further particular embodiment the invention relates to compounds of formula (I), wherein $R^3$ is selected from pyridine, pyrazine, pyrimidine, imidazole, oxazole, quinoxaline, quinazoline, optionally substituted by 1 to 3 substituents selected from halogen, $C_1$-$C_7$-alkyl, $C_1$-$C_7$ alkoxy, aryl, heteroaryl, $NR^5R^6$, —O—$R^7$ or $R^3$ is selected from the group consisting of:

a)

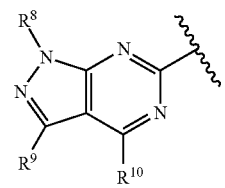

b)

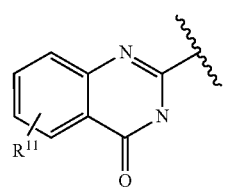

c)

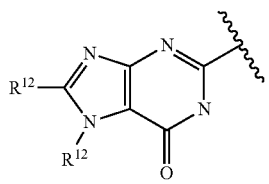

d)

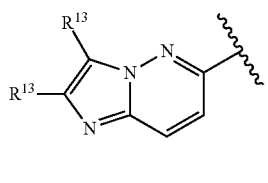

e)

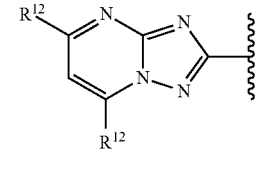

f)

g)

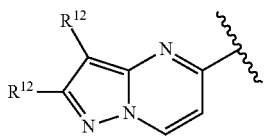

$R^8$, $R^9$ and $R^{10}$ are independently selected from hydrogen, $C_1$-$C_7$-alkyl and $NR^5R^6$, $R^{11}$ is selected from hydrogen, halogen, $C_1$-$C_7$-alkyl, $C_1$-$C_7$ alkoxy, $R^{12}$ is selected from hydrogen or $C_1$-$C_7$-alkyl, $R^{13}$ is selected from hydrogen, $C_1$-$C_7$-alkyl optionally substituted by halogen, $C_3$-$C_8$ cycloalkyl, —C(O)—$NH_2$.

In a further particular embodiment the invention relates to compounds of formula (I), wherein $R^3$ is selected from pyridine, pyrazine, pyrimidine, imidazole, oxazole, quinoxaline, quinazoline, optionally substituted by 1 to 3 substituents selected from halogen, $C_1$-$C_7$-alkyl, $C_1$-$C_7$ alkoxy, aryl, heteroaryl, $NR^5R^6$, —O—$R^7$ or $R^3$ is selected from the group consisting of:

a)

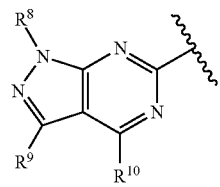

b)

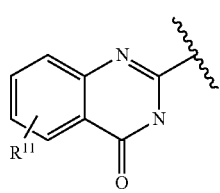

c)

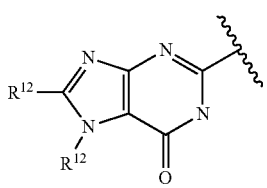

d)

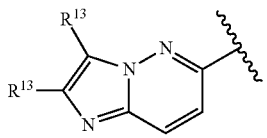

e)

f)

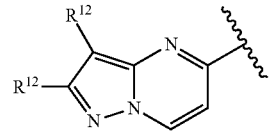

Particular compounds of the present invention are selected from the group consisting of:
(E)-2-[2-(4-Methyl-6-pyrrolidin-1-yl-pyrimidin-2-yl)-vinyl]-quinoline
(E)-4-(6-(2-(4-methoxy-3,5-dimethylpyridin-2-yl)vinyl) pyridin-2-yl)morpholine
(E)-4-methoxy-3,5-dimethyl-2-(2-(6-(pyrrolidin-1-yl)pyridin-2-yl)vinyl)pyridine
Methyl-{6-[2-(1-methyl-4-phenyl-1H-imidazol-2-yl)-ethyl]-pyridin-2-yl}-amine
4-methoxy-3,5-dimethyl-2-(2-(6-(pyrrolidin-1-yl)pyridin-2-yl)ethyl)pyridine
2-(2-(1-methyl-4-phenyl-1H-imidazol-2-yl)ethyl)-6-(pyrrolidin-1-yl)pyridine
4-(6-(2-(1-methyl-4-phenyl-1H-imidazol-2-yl)ethyl)pyridin-2-yl)morpholine
2,3,5-trimethyl-6-(2-(6-(pyrrolidin-1-yl)pyridin-2-yl)ethyl) pyrazine
2-methyl-3-((6-(pyrrolidin-1-yl)pyridin-2-yl)methoxy)quinoxaline
2-Methyl-3-[(E)-2-(6-pyrrolidin-1-yl-pyridin-2-yl)-vinyl]-quinoxaline
2-Methyl-3-[2-(6-pyrrolidin-1-yl-pyridin-2-yl)-ethyl]-quinoxaline
2-[2-(5-Methyl-2-phenyl-oxazol-4-yl)-ethyl]-6-pyrrolidin-1-yl-pyridine
4-(6-chloro-2-((6-(pyrrolidin-1-yl)pyridin-2-yl)methoxy) quinazolin-4-yl)morpholine
2-(2-(1-methyl-4-phenyl-1H-imidazol-2-yl)ethyl)-6-(pyrazolidin-1-yl)pyrazine
2-methyl-3-((6-(piperidin-1-yl)pyridin-2-yl)methoxy)quinoxaline
4-(2-((6-(pyrrolidin-1-yl)pyridin-2-yl)methoxy)quinazolin-4-yl)morpholine
6-chloro-N,N-dimethyl-2-((6-(pyrrolidin-1-yl)pyridin-2-yl) methoxy)quinazolin-4-amine
4-(1-methyl-6-((6-(pyrrolidin-1-yl)pyridin-2-yl)methoxy)-1H-pyrazolo[3,4-d]pyrimidin-4-yl)morpholine
(E)-4-(6-chloro-2-(2-(6-(pyrrolidin-1-yl)pyridin-2-yl)vinyl) quinazolin-4-yl)morpholine
4-(6-chloro-2-(2-(6-(pyrrolidin-1-yl)pyridin-2-yl)ethyl)quinazolin-4-yl)morpholine
4-(2-(2-(6-(pyrrolidin-1-yl)pyridin-2-yl)ethyl)quinazolin-4-yl)morpholine
6-chloro-2-((6-(pyrrolidin-1-yl)pyridin-2-yl)methoxy)-4-(tetrahydro-2H-pyran-4-yloxy)quinazoline
4-[2-(2H-Pyrazol-3-yl)-6-(6-pyrrolidin-1-yl-pyridin-2-ylmethoxy)-pyrimidin-4-yl]-morpholine
4-(2-(pyridin-3-yl)-6-((6-(pyrrolidin-1-yl)pyridin-2-yl) methoxy)pyrimidin-4-yl)morpholine
(E)-(1-(6-(2-(6-chloro-4-(dimethylamino)quinazolin-2-yl) vinyl)pyridin-2-yl)pyrrolidin-3-yl)methanol
5-chloro-2-(2-(6-(pyrrolidin-1-yl)pyridin-2-yl)ethyl)quinazolin-4(3H)-one
6-chloro-5-methoxy-2-(2-(6-(pyrrolidin-1-yl)pyridin-2-yl) ethyl)quinazolin-4(3H)-one
7,8-dimethyl-2-(2-(6-(pyrrolidin-1-yl)pyridin-2-yl)ethyl)-1H-purin-6(7H)-one 6-chloro-2-(2-(6-(pyrrolidin-1-yl)pyridin-2-yl)ethyl)qui-
nazolin-4(3H)-one
2-(2-(6-(2,5-dimethylpyrrolidin-1-yl)pyridin-2-yl)ethyl)-N,
N-dimethylquinazolin-4-amine
1-(6-(2-(6-chloro-4-(dimethylamino)quinazolin-2-yl)ethyl)
pyridin-2-yl)pyrrolidin-3-ol
1-(6-(2-(4-(dimethylamino)quinazolin-2-yl)ethyl)pyridin-2-
yl)pyrrolidin-3-01
(1-(6-(2-(6-chloro-4-(dimethylamino)quinazolin-2-yl)ethyl)
pyridin-2-yl)pyrrolidin-3-yl)methanol
(1-(6-(2-(4-(dimethylamino)quinazolin-2-yl)ethyl)pyridin-
2-yl)pyrrolidin-3-yl)methanol
(E)-6-chloro-N,N-dimethyl-2-(2-(6-(2-methylpyrrolidin-1-
yl)pyridin-2-yl)vinyl)quinazolin-4-amine
(E)-1-(6-(2-(6-chloro-4-(dimethylamino)quinazolin-2-yl)vi-
nyl)pyridin-2-yl)pyrrolidin-2-one
8-methyl-2-(2-(6-(pyrrolidin-1-yl)pyridin-2-yl)ethyl)qui-
nazolin-4(3H)-one
6-chloro-N,N-dimethyl-2-(2-(6-(2-methylpyrrolidin-1-yl)
pyridin-2-yl)ethyl)quinazolin-4-amine
(E)-2-((6-(2-(6-chloro-4-(dimethylamino)quinazolin-2-yl)
vinyl)pyridin-2-yl)(methyl)amino)ethanol
2-((6-(2-(6-chloro-4-(dimethylamino)quinazolin-2-yl)ethyl)
pyridin-2-yl)(methyl)amino)ethanol
(E)-6-chloro-2-(2-(6-(dimethylamino)pyridin-2-yl)vinyl)-
N,N-dimethylquinazolin-4-amine
6-chloro-2-(2-(6-(dimethylamino)pyridin-2-yl)ethyl)-N,N-
dimethylquinazolin-4-amine
(E)-5,8-dimethyl-2-(2-(6-(pyrrolidin-1-yl)pyridin-2-yl)vi-
nyl)-[1,2,4]triazolo[1,5-a]pyrazine
2,3-dimethyl-6-((6-(pyrrolidin-1-yl)pyridin-2-yl)methoxy)
imidazo[1,2-b]pyridazine
5,8-dimethyl-2-(2-(6-(pyrrolidin-1-yl)pyridin-2-yl)ethyl)[1,
2,4]triazolo[1,5-a]pyrazine
5,7-dimethyl-2-(2-(6-(pyrrolidin-1-yl)pyrazin-2-yl)ethyl)-
[1,2,4]triazolo[1,5-a]pyrimidine
(E)-5,7-dimethyl-2-(2-(6-(pyrrolidin-1-yl)pyridin-2-yl)vi-
nyl)[1,2,4]triazolo[1,5-a]pyrimidine
5,7-Dimethyl-2-[2-(6-pyrrolidin-1-yl-pyridin-2-yl)-ethyl]-
[1,2,4]triazolo[1,5-a]pyrimidine
2,3-dimethyl-6-(2-(6-(pyrrolidin-1-yl)pyridin-2-yl)ethyl)
imidazo[1,2-b]pyridazine
(E)-5,8-dimethyl-2-(2-(6-(pyrrolidin-1-yl)pyrazin-2-yl)vi-
nyl)-[1,2,4]triazolo[1,5-a]pyrazine
5,8-dimethyl-2-(2-(6-(pyrrolidin-1-yl)pyrazin-2-yl)ethyl)-
[1,2,4]triazolo[1,5-a]pyrazine
2-ethyl-3-methyl-6-((6-(pyrrolidin-1-yl)pyridin-2-yl)
methoxy)imidazo[1,2-b]pyridazine
2,3-dimethyl-5-((6-(pyrrolidin-1-yl)pyridin-2-yl)methoxy)
pyrazolo[1,5-a]pyrimidine
2-methyl-6-((6-(pyrrolidin-1-yl)pyridin-2-yl)methoxy)imi-
dazo[1,2-b]pyridazine
2-cyclopropyl-6((6-(pyrrolidin-1-yl)pyridin-2-yl)methoxy)
imidazo[1,2-b]pyridazine
3-methyl-6-((6-(pyrrolidin-1-yl)pyridin-2-yl)methoxy)imi-
dazo[1,2-b]pyridazine-2-carboxamide
3-methyl-N-((6-(pyrrolidin-1-yl)pyridin-2-yl)methyl)-2-
(trifluoromethyl)imidazo[1,2-b]pyridazin-6-amine
2,3-dimethyl-5-(2-(6-(pyrrolidin-1-yl)pyridin-2-yl)ethyl)
pyrazolo[1,5-a]pyrimidine Yet particular compounds of the present invention are selected from the group consisting of:
2-methyl-3-((6-(pyrrolidin-1-yl)pyridin-2-yl)methoxy)qui-
noxaline
4-(6-chloro-2-(2-(6-(pyrrolidin-1-yl)pyridin-2-yl)ethyl)qui-
nazolin-4-yl)morpholine
6-chloro-2-(2-(6-(pyrrolidin-1-yl)pyridin-2-yl)ethyl)qui-
nazolin-4(3H)-one
5,8-dimethyl-2-(2-(6-(pyrrolidin-1-yl)pyridin-2-yl)ethyl)[1,
2,4]triazolo[1,5-a]pyrazine.

The invention further relates to a process for the manufacture of compounds of formula (I) as defined above, wherein B is $C_1$-$C_4$ alkylene or $C_2$-$C_4$ alkenylene, which process comprises:

a) reacting a compound of formula (III)
with

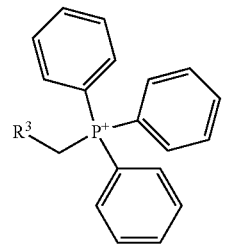

(III)

b) a compound of formula (IV)

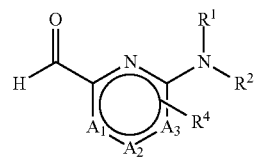

IV to give a compound of formula Ia

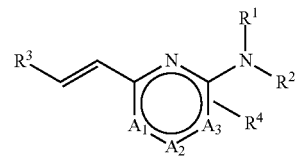

(Ia)

and optionally hydrogenation of compound of formula Ia to a compound of formula Ib

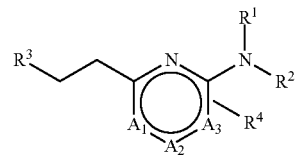

(Ib)

wherein $A_1$, $A_2$, $A_3$, $R^1$, $R^2$, $R^3$ and $R^4$ are as defined above and, if desired, converting the compounds into pharmaceutically acceptable salts thereof.

The invention further relates to a process for the manufacture of compounds of formula (I) as defined above, wherein B is $C_1$-$C_4$ alkylene or $C_2$-$C_4$ alkenylene, which process comprises:

a) reacting a compound of formula VI

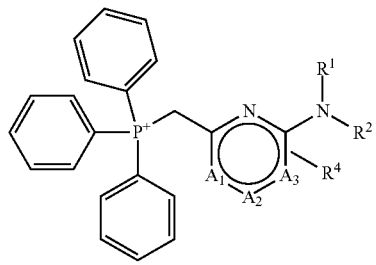
(VI)

b) with a compound of formula VII

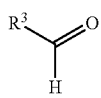
(VII)

c) to give a compound of formula Ia

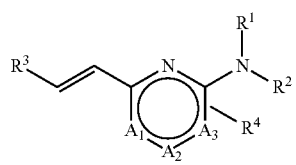
(Ia)

and optionally hydrogenation of compound of formula Ia to a compound of formula Ib

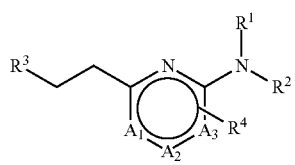
(Ib)

wherein $A_1$, $A_2$, $A_3$, $R^1$, $R^2$, $R^3$ and $R^4$ are as defined above and, if desired, converting the compounds into pharmaceutically acceptable salts thereof.

The invention further relates to a process for the manufacture of compounds of formula (I) as defined above, wherein B is —O—$C_1$-$C_4$ alkyl, which process comprises:

a) reacting a compound of formula XIII

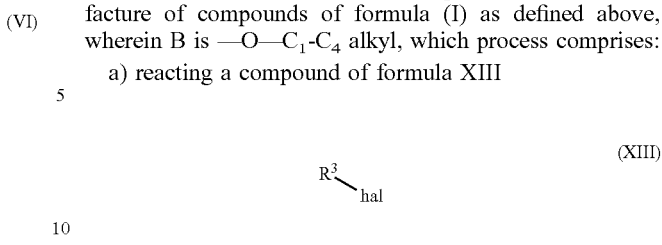
(XIII)

b) with a compound of formula XVI

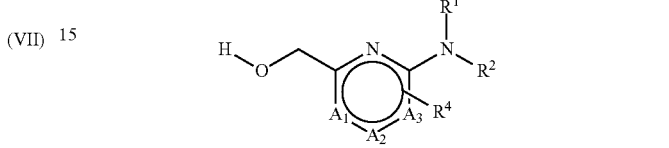
(XVI)

c) to a compound of formula Ic

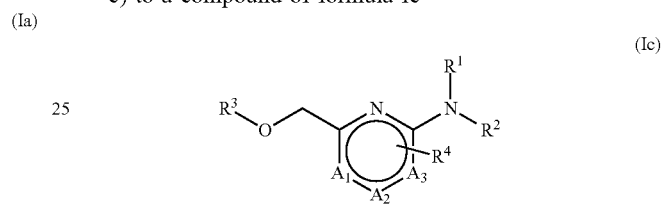
(Ic)

wherein hal is halogen, $A_1$, $A_2$, $A_3$, $R^1$, $R^2$, $R^3$ and $R^4$ are as defined above and, if desired, converting the compounds into pharmaceutically acceptable salts thereof.

The reaction described above can be carried out under conditions as described in the description and examples or under conditions well known to the person skilled in the art.

The present invention also relates to compounds of formula (I) as defined above, when prepared by a process as described above.

Synthetic Procedures

Compounds of general formula (I) wherein B is $C_2$-alkylene or $C_2$-alkenylene can be prepared as outlined in Schemes 1 to 6.

Scheme 1

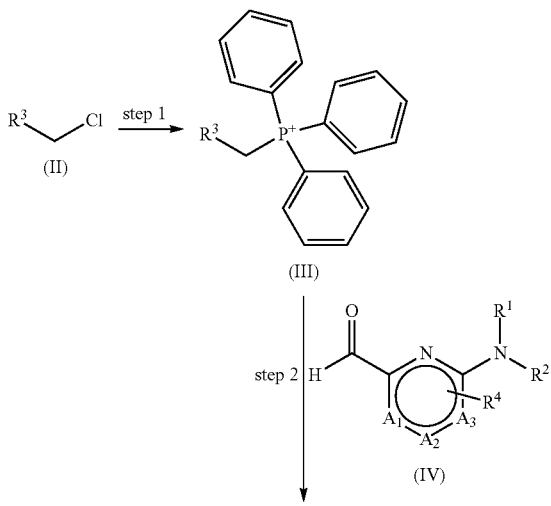

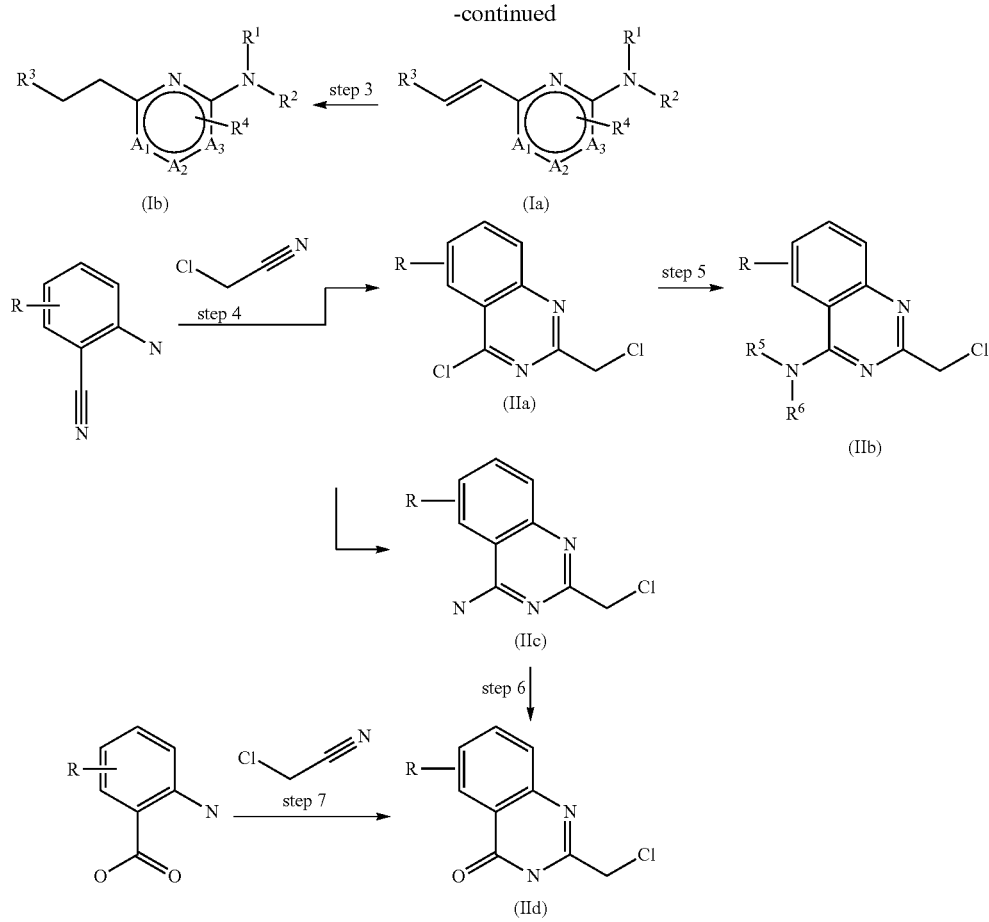

Compounds of formula (II), (III) and (IV) are commercial or can be prepared as described below or by literature-known methods. Compounds of formula (Ia) can be prepared by a Wittig reaction (step 2) in the presence of a base such as DBU in a solvent such as THF, EtOH or mixtures thereof. Compounds of formula (Ib) are obtained by subsequent hydrogenation (step 3) at ambient pressure (balloon) using a catalyst such as Pd/C or Raney nickel in a solvent such as EtOH or MeOH (Scheme 1).

Compounds of formula (IIa) can be prepared by treating a 2-aminobenzonitrile with 2-chloroacetonitrile in dioxane at 0° C. in the presence of a stream of HCl which is passed throughout the solution for 7 hrs (step 4). Compounds of formula (IIb) are then obtained by treatment with an amine $HNR^5R^6$ in a solvent such as THF at r.t. (step 5).

Sometimes, aminoquinazolines of formula (IIc) are formed as side product or main product when reacting a 2-aminobenzonitrile with 2-chloroacetonitrile (step 4). Compounds of formula (IIc) can be converted to the corresponding quinazolones (IId) by hydrolysis in 6N HCl at 95° C. or by diazotization and hydrolysis with sodium nitrite in HOAc/$H_2O$ at 65° C. (step 6). Quinazolones (IId) can alternatively be obtained reacting a 2-aminobenzoic acid with 2-chloroacetonitrile in the presence of NaOMe in MeOH at r.t. (step 7).

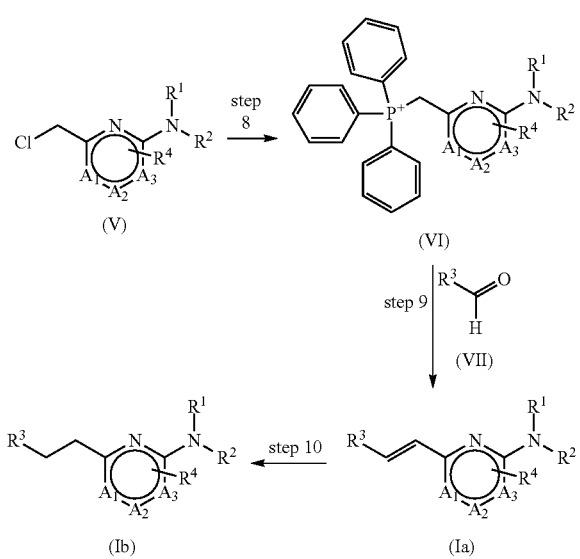

Compounds of formula (Ia) and (Ib) can alternatively obtained by reversing the position of the reactive groups required for the Wittig reactions, condensing intermediates (VI) and (VII) instead of (III) and (IV) (Scheme 2).

Scheme 3

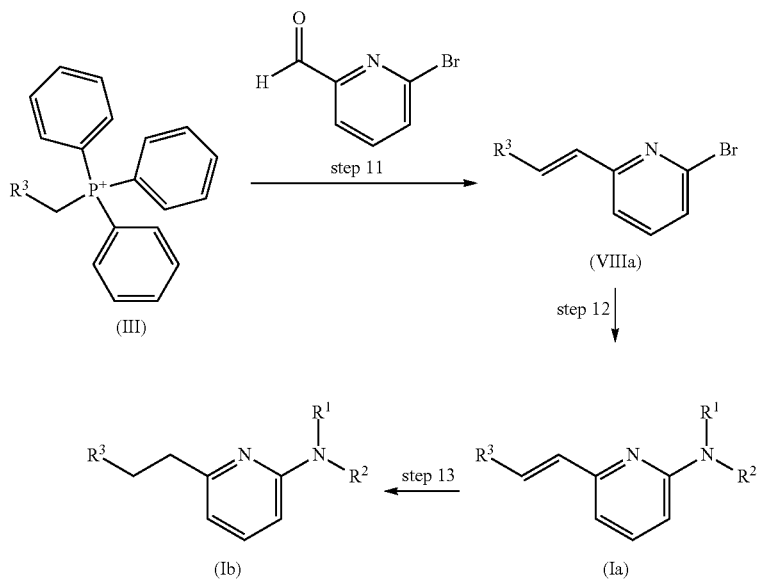

Compounds of formula (Ia) can also be prepared via bromopyridine intermediates of formula (VIIIa) which can be obtained by the Wittig chemistry described in scheme 1 from intermediate (III) and 6-bromo-pyridinecarbaldehyde. Reacting intermediates of formula (VIIIa) with a secondary amine or with 2-pyrrolidinone under Buchwald conditions, e.g. using Xantphos as ligand, Pd(OAc)$_2$ as Pd source, aqueous K$_2$CO$_3$ as base and xylene as solvent, refluxing the reaction mixture over night provides alkenes of formula (Ia).

Alternatively, compounds of formula (VIIIa) can be treated by a secondary amine or a secondary ammonium salt in a solvent such as DMF and in the presence of a base such as diisopropyl-ethyl amine at a temperature of 120° C. (step 12).

Compounds of formula (Ib) are obtained from intermediate (Ia) by subsequent hydrogenation (step 13) at ambient pressure (balloon) using a catalyst such as Pd/C or Raney nickel in a solvent such as EtOH or MeOH (Scheme 3).

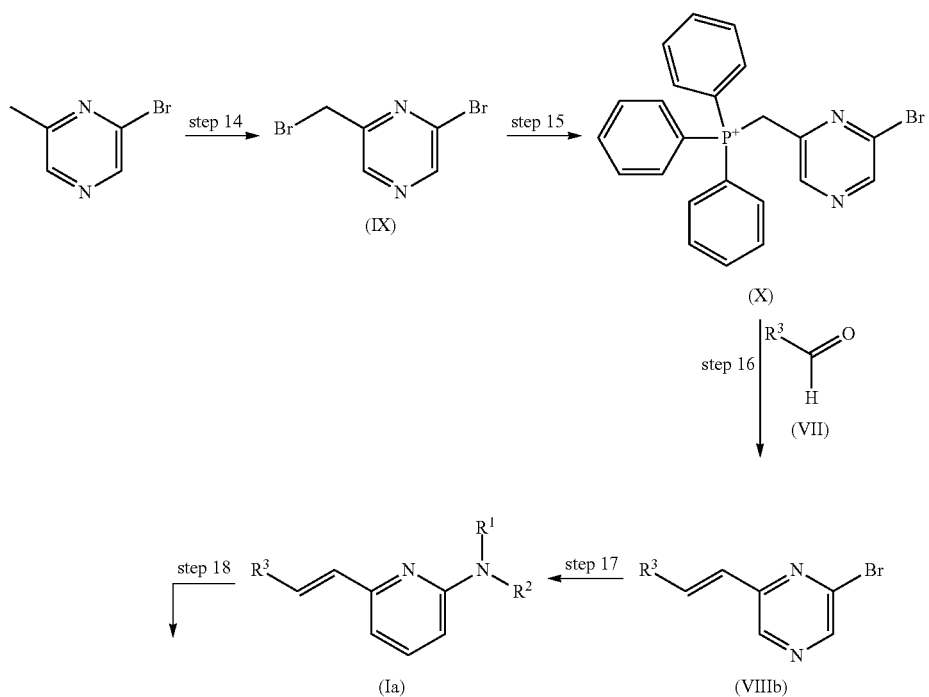

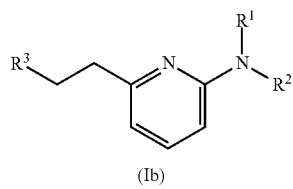

(Ib)

Bromopyrazine intermediates of formula (VIIIb) can be obtained by side chain bromination of a suitable methyl precursor with NBS in the presence of benzoyl peroxide as catalyst and carbon tetrachloride as solvent (step 14). The conversion of bromomethyl intermediate (IX) via Wittig salt (X) which is condensed with aldehyde (VII) to provide compounds (Ia) and (Ib) (steps 15-18) proceeds then in analogy to the procedures described previously (Scheme 4).

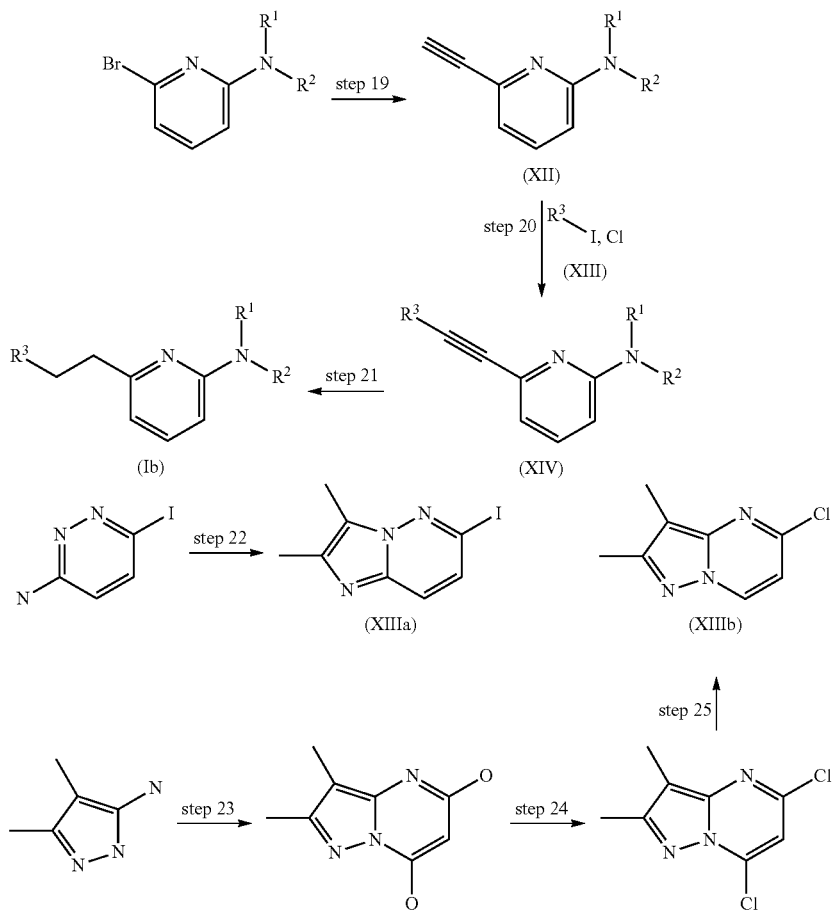

Scheme 5

Compounds of formula (I) can be prepared by reacting an alkyne of formula (XII) with a aromatic halogenide of formula (XIII) under Sonogashira conditions using a copper catalyst such as copper(I) iodide and a palladium catalyst such as bis(triphenylphosphine)palladium(II) dichloride, a base such as triethylamine and a solvent such as DMF at 80° C. overnight. Compounds of formula (I) are obtained from intermediate (XIV) by hydrogenation (step 3) at ambient pressure (balloon) using a catalyst such as Pd/C in a solvent such as EtOH or MeOH.

An iodide of formula (XIIIa) can be prepared by refluxing 2-amino-5-iodopyridazine with an α-haloketone in a solvent such as EtOH or 1,2-dimethoxyethane. Alternatively, a chloride of formula (XIIIb) can be prepared according to procedures described in WO2006/128692.

Scheme 6

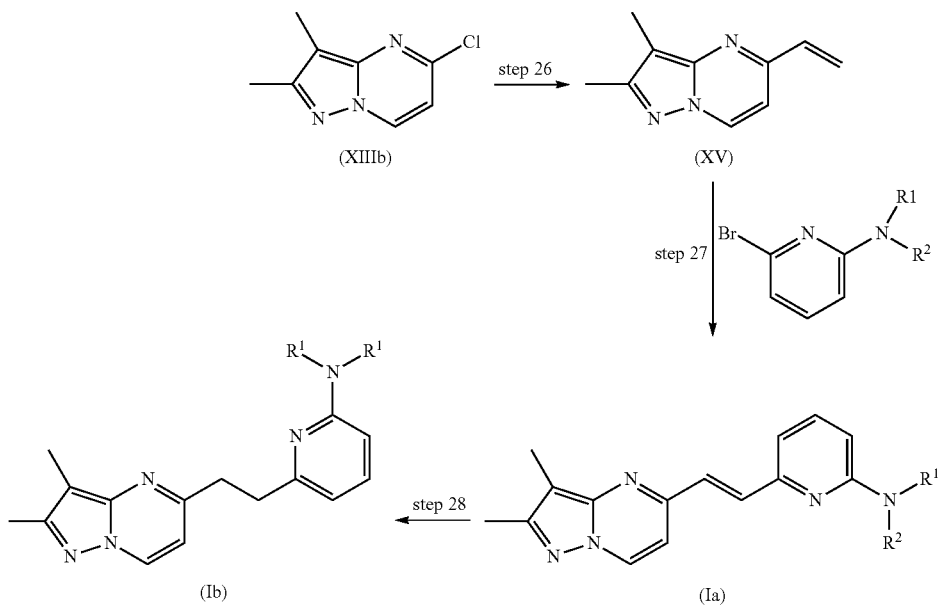

Compounds of formula (Ia) can be obtained by Heck reaction between an alkene of formula (XV) and 2-bromo-6-pyrolidine-pyridine (step 27), using a catalytic Pd source such as Pd(OAc)$_2$, a phosphine such as tri-(o-tolyl)phosphine as ligand, a base such as triethylamine and a solvent such as DMF.

Compounds of formula (Ia) are obtained by subsequent hydrogenation (step 28) at ambient pressure (balloon) using a catalyst such as Pd/C or Raney nickel in a solvent such as EtOH or MeOH.

Compounds of general formula (I) wherein B is —O—C$_1$-C$_4$ alkyl can be prepared as outlined in Scheme 7.

Scheme 7

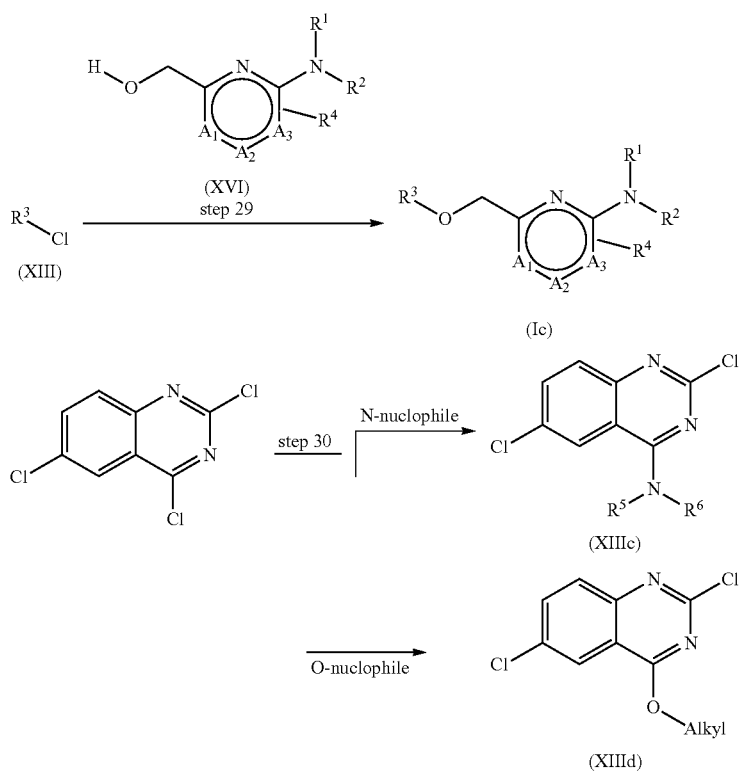

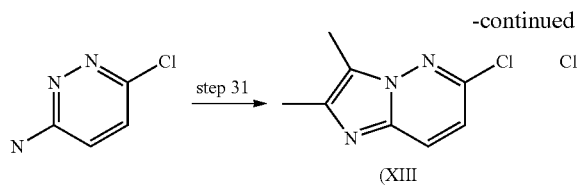 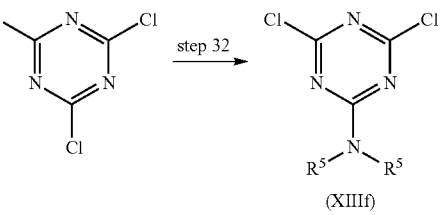

Compounds of formula (Ic) are prepared by reaction of an aromatic chloride of formula (XIII) and an alcohol of formula (XVI) (step 29), which is previously deprotonated by a base such as NaH in a solvent such as DMF (Scheme 5). The reaction takes 2 hrs to 24 hrs at a temperature between 0° C. and r.t. Intermediates (XIII) are commercial or can be prepared as described below or by methods known from the literature.

Intermediates of formula (XIIIc) and (XIIId) can be prepared e.g. by substitution of 2,4,6-trichloroquinazoline by an N- or O-nucleophile (step 30). N-Nucleophiles are for example amines or ammonium salts which are reacted with 2,4,6-trichloroquinazoline in a solvent such as chloroform in the presence of a base such as triethylamine. O-Nucleophiles are for example aliphatic alcohols which are deprotonated before adding them to the quinazoline intermediate with a base such as NaH in a solvent such as DMF before adding them to the quinazoline intermediate.

Intermediates of type (XIIIe) are prepared by refluxing 2-amino-5-chloropyridazine with an α-haloketone in a solvent such as EtOH (step 31).

Intermediates of formula (XIIIf) are prepared by reaction of 2,4,6-trichlorotriazine with a secondary amine in a solvent such as CHCl$_3$, THF or dioxane in the presence of a base such as triethylamine at r.t. (step 32).

Another starting material for the preparation of compounds of formula (Ic) is the aromatic chloride (XIIIb) described on Scheme 5.

The invention therefore also relates to compounds as described above for use as therapeutically active substance.

The invention also relates to pharmaceutical compositions comprising a compound as described above and a therapeutically inert carrier.

In another embodiment, the invention relates to the use of a compound as described above for the treatment or prophylaxis of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma or breast cancer.

Yet in another embodiment, the invention relates to the use of a compound as described above for the preparation of a medicament for the treatment or prophylaxis of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma or breast cancer.

The invention also relates to a compound as described above for the treatment or prophylaxis of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma or breast cancer.

The invention further relates to a compound as described above, when manufactured according to a process as described above.

In another embodiment, the invention relates to a method for the treatment or prophylaxis of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma or breast cancer, which method comprises administering an effective amount of a compound as described above.

Prevention and/or treatment of schizophrenia is a particular indication. Yet particular indication is prevention and/or treatment of positive, negative and/or cognitive symptoms associated with schizophrenia.

The invention further relates to a pharmaceutical composition comprising compounds of formula (I) as defined above and a therapeutically inert carrier.

As described above, the novel compounds of the present invention have been found to inhibit PDE10A activity. The compounds of the present invention can therefore be used, either alone or in combination with other drugs, for the treatment or prophylaxis of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma or breast cancer.

Yet in another embodiment, the invention relates to the use of a compound of the present invention for the preparation of a medicament for the treatment or prophylaxis of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma or breast cancer.

The invention also relates to a compound as described above for the treatment or prophylaxis of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma or breast cancer.

The compounds of formula (I) can have one or more asymmetric C atoms and can therefore exist as an enantiomeric mixture, mixture of stereoisomers or as optically pure compounds. The compounds of formula (I) include all diastereomers, tautomers, racemates and mixtures thereof.

Particular compounds of formula (I) are described in the examples as individual compounds as well as pharmaceutically acceptable salts as well as pharmaceutically acceptable esters thereof. Furthermore, the substituents as found in the specific examples described below, individually constitute particular embodiments of the present invention.

Pharmaceutical Compositions and Administration

Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compounds of formula (I) are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to inhibit PDE10 and to control the cAMP signaling pathway. For example, such amount may be below the amount that is toxic to normal cells, or the mammal as a whole.

In one example, the pharmaceutically effective amount of the compound of the invention administered parenterally per dose will be in the range of about 0.01-100 mg/kg, alternatively about 0.1 to 20 mg/kg of patient body weight per day, with the typical initial range of compound used being 0.3 to 15 mg/kg/day. In another embodiment, oral unit dosage forms, such as tablets and capsules, preferably contain from about 25-100 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 25 mg, 50 mg, 100 mg, 250 mg, or 500 mg of the compound of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5-400 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

An embodiment, therefore, includes a pharmaceutical composition comprising a compound of Formula (I), or a stereoisomer or pharmaceutically acceptable salt thereof. In a further embodiment includes a pharmaceutical composition comprising a compound of Formula (I), or a stereoisomer or pharmaceutically acceptable salt thereof, together with a pharmaceutically acceptable carrier or excipient.

The following test was carried out in order to determine the activity of the compounds of the present invention. PDE10 activity of the compounds of the present invention was determined using a Scintillation Proximity Assay (SPA)-based method similar to the one previously described (Fawcett, L. et al., Proc Natl Acad Sci USA (2000) 97(7): 3702-3707).

The human PDE10A full length assay was performed in 96-well micro titer plates. The reaction mixture of 50 µl contained 20 mM HEPES pH=7.5/10 mM MgCl2/0.05 mg/ml BSA (Sigma cat. #A-7906), 50 nM cGMP (Sigma, cat. #G6129) and 50 nM [3H]-cGMP (GE Healthcare, cat. #TRK392 S.A. 13.2 Ci/mmol), 3.75 ng/well PDE10A enzyme (Enzo Life Science, Lausen, Switzerland cat #SE-534) with or without a specific test compound. A range of concentrations of the potential inhibitor was used to generate data for calculating the concentration of inhibitor resulting in 50% of the effect (e.g. IC50, the concentration of the competitor inhibiting PDE10A activity by 50%). Non-specific activity was tested without the enzyme. The reaction was initiated by the addition of the substrate solution (cGMP and [3H]-cGMP) and allowed to progress for 20 minutes at room temperature. The reaction was terminated by adding 25 µl of YSi-SPA scintillation beads (GE Healthcare, cat. #RPNQ0150) in 18 mM zinc sulphate solution (stop reagent). After 1 h under shaking, the plate was centrifuged one minute at 170 g to allow beads to settle. Afterwards, radioactive counts were measured on a Perkin Elmer Top-Count Scintillation plate reader.

The compounds according to formula (I) have an $IC_{50}$ value below 10 µM, more specifically below 5 µM, yet more specifically below 1 µM. The following table shows data for some examples.

| Example | $IC_{50}$ [µM] |
| --- | --- |
| 1 | 0.53 |
| 2 | 8.0 |
| 3 | 0.79 |
| 4 | 4.06 |
| 5 | 0.61 |
| 6 | 1.84 |
| 7 | 3.14 |
| 8 | 0.60 |
| 9 | 0.03 |
| 10 | 0.09 |
| 11 | 0.12 |
| 12 | 2.00 |
| 13 | 0.0025 |
| 14 | 0.12 |
| 15 | 1.68 |
| 16 | 0.05 |
| 17 | 0.007 |
| 18 | 0.276 |
| 19 | 0.0063 |
| 20 | 0.0033 |
| 21 | 0.046 |
| 22 | 0.094 |
| 23 | 1.08 |
| 24 | 1.63 |
| 25 | 0.22 |
| 26 | 0.40 |
| 27 | 0.47 |
| 28 | 2.73 |
| 29 | 0.10 |
| 30 | 2.30 |
| 31 | 0.77 |
| 32 | 0.48 |
| 33 | 0.15 |
| 34 | 1.63 |
| 35 | 0.027 |
| 36 | 0.82 |
| 37 | 3.27 |
| 38 | 0.081 |
| 39 | 0.24 |
| 40 | 2.16 |
| 41 | 0.75 |
| 42 | 1.68 |
| 43 | 0.012 |
| 44 | 0.16 |
| 45 | 0.0045 |
| 46 | 0.30 |
| 47 | 0.031 |
| 48 | 0.11 |
| 49 | 0.63 |
| 50 | 0.018 |
| 51 | 0.14 |
| 52 | 0.54 |
| 53 | 0.069 |
| 54 | 0.26 |
| 55 | 0.60 |
| 56 | 1.05 |
| 57 | 0.20 |
| 58 | 0.30 |

EXAMPLES

Example 1

(E)-2-[2-(4-Methyl-6-pyrrolidin-1-yl-pyrimidin-2-yl)-vinyl]-quinoline

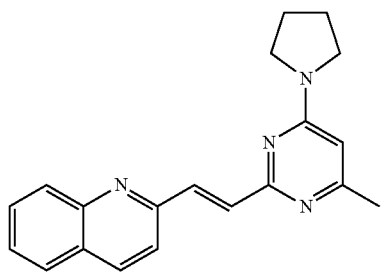 [SMILES: Cc1cc(N2CCCC2)nc(/C=C/c2ccc3ccccc3n2)n1]

Step 1:
2-Chloro-4-methyl-6-pyrrolidin-1-yl-pyrimidine

To a solution of 2,4-dichloro-6-methylpyridine (815 mg, 5 mmol) in isopropanol (5 ml) was slowly added pyrolidine (0.83 ml, 10 mmol), maintaining the temperature at r.t. using a water bath. After 45 min, the resulting suspension was concentrated. The crude product was purified by silica gel chromatography using CH$_2$Cl$_2$/EtOAc 4:1 as eluent, providing the title compound (723 mg, 73%) as yellow solid.

Step: E)-2-[2-(4-Methyl-6-pyrrolidin-1-yl-pyrimidin-2-yl)-vinyl]-quinoline

To a suspension of tris(dibenzylidenacetone)dipalladium (0) (14 mg, 0.014 mmol) and cesium carbonate (330 mg, 1.01 mmol) in DMF (1 ml) were added 2-chloro-4-methyl-6-pyrrolidin-1-yl-pyrimidine (183 mg, 0.92 mmol) in DMF (1 ml), 2-vinylquinoline (284 mg, 1.83 mmol) in DMF (0.3 ml) and tri-tert-butyl-phosphane (0.011 g, 0.055 mmol) in DMF (0.5 ml). The solution was heated overnight to 130° C., then cooled to r.t. and taken up in CH$_2$Cl$_2$. The solids were filtered off, the filtrate was concentrated. The crude product was purified by silica gel chromatography using CH2Cl2/EtOAc 4:1 as eluent to provide the title compound (126 mg, 45%) as reddish solid.

Example 2

(E)-4-(6-(2-(4-Methoxy-3,5-dimethylpyridin-2-yl)vinyl)pyridin-2-yl)morpholine

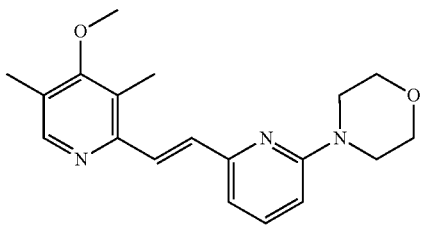 [SMILES: COc1c(C)cnc(/C=C/c2cccc(N3CCOCC3)n2)c1C]

Step 1: (4-Methoxy-3,5-dimethyl pyridin-2 ylmethyl)-triphenyl phosphonium chloride To a stirred solution of 2-(chloromethyl)-4-methoxy-3,5-dimethylpyridine hydrochloride (0.6 g, 2.7 mmol) at r.t. in THF (10 ml) and ethanol (10.0 ml) under an argon atmosphere was added triphenylphosphine (709 mg, 2.7 mmol). The mixture was stirred at 75° C. for 17 hrs. The mixture was cooled to r.t. and concentrated to leave the crude product as an off-white foam (1.3 g). The crude product was directly used in the next step.
MS: M=412.3 (M+H)+

Step 2: (E)-4-(6-(2-(4-Methoxy-3,5-dimethylpyridin-2-yl)vinyl)pyridin-2-yl)morpholine To a stirred mixture of the crude ((4-methoxy-3,5-dimethylpyridin-2-yl)methyl)triphenylphosphonium chloride hydrochloride (1.31 g, 1.35 mmol) and DBU (515 mg, 510 µl, 3.38 mmol) at r.t. in THF (15 ml) under an argon atmosphere was added 3-phenyl-1,2,4-oxadiazole-5-carbaldehyde (235 mg, 1.35 mmol) in one portion. The mixture was stirred at r.t. overnight. The mixture was diluted with EtOAc and washed with 10% aq. Na$_2$CO$_3$ solution. The aqueous phase was back extracted with EtOAc. The combined organics were washed with brine, dried over MgSO$_4$, filtered and evaporated. The crude product was purified by chromatography on silica gel using a heptane/EtOAc gradient as eluent, providing the title compound (265 mg, 30% over two steps) as yellow solid.
MS: M=326.3 (M+H)+

Example 3

(E)-4-methoxy-3,5-dimethyl-2-(2-(6-(pyrrolidin-1-yl)pyridin-2-yl)vinyl)pyridine

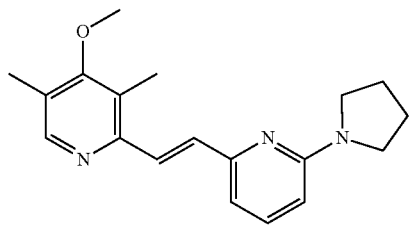 [SMILES: COc1c(C)cnc(/C=C/c2cccc(N3CCCC3)n2)c1C]

According to the procedures described in step 2 of example 2, the title compound was prepared using 6-(pyrrolidin-1-yl)picolinaldehyde. Yellow solid
MS: M=310.2 (M+H)+

Example 4

Methyl-{6-[2-(1-methyl-4-phenyl-1H-imidazol-2-yl)-ethyl]-pyridin-2-yl}-amine

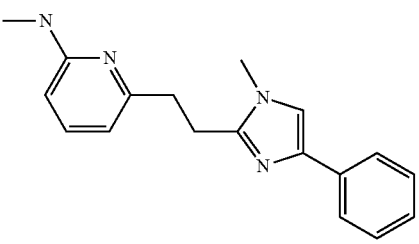 [SMILES: CNc1cccc(CCc2nc(-c3ccccc3)cn2C)n1]

Using similar procedures as described in examples 2 and 5, the title compound was prepared using (6-chloromethyl-pyridin-2-yl)-methyl-amine as starting material in the 1st step (preparation of the Wittig salt) and 1-methyl-4-phenyl-1H-imidazole-2-carb aldehyde (CAS 123511-51-3) in the 2nd step (Wittig reaction). Off-white solid.

MS: M=293 (M+H)+

Example 5

4-Methoxy-3,5-dimethyl-2-(2-(6-(pyrrolidin-1-yl)pyridin-2-yl)ethyl)pyridine

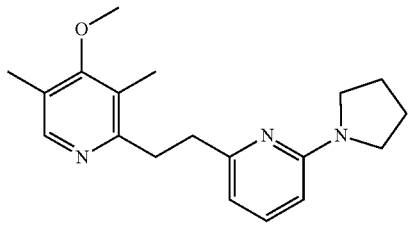 [SMILES: COc1c(C)cnc(CCc2cccc(N3CCCC3)n2)c1C]

To a stirred solution of (E)-4-methoxy-3,5-dimethyl-2-(2-(6-(pyrrolidin-1-yl)pyridin-2-yl)vinyl)pyridine (example 3; 0.172 g, 556 μmol) in ethanol (5 ml) was added 10% Pd/C (24 mg). The reaction mixture was hydrogenated overnight (balloon). The catalyst was filtered off and washed with EtOH. The filtrate was evaporated. The crude product was purified by chromatography using a CH₂Cl₂/MeOH gradient as eluent, providing the title compound (0.07 g, 40%) as light yellow viscous oil.

MS: M=312.2 (M+H)+

Example 6

2-(2-(1-Methyl-4-phenyl-1H-imidazol-2-yl)ethyl)-6-(pyrrolidin-1-yl)pyridine

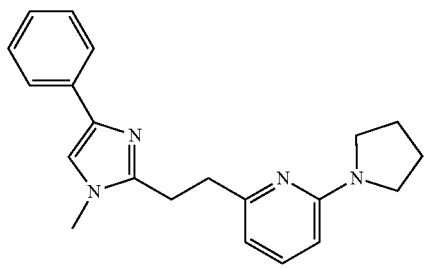 [SMILES: Cn1cc(-c2ccccc2)nc1CCc1cccc(N2CCCC2)n1]

According to the procedures described in examples 2 and 5, the title compound was prepared using 2-chloromethyl-1-methyl-4-phenyl-1H-imidazole (CAS 1201687-66-2) as starting material in the 1st step (preparation of the Wittig salt) and 6-(pyrrolidin-1-yl)picolinaldehyde in the 2nd step (Wittig reaction). Colorless viscous oil.

MS: M=333.5 (M+H)+

Example 7

4-(6-(2-(1-Methyl-4-phenyl-1H-imidazol-2-yl)ethyl)pyridin-2-yl)morpholine

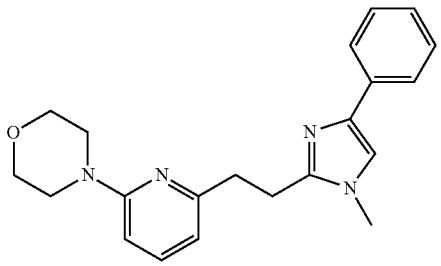 [SMILES: Cn1cc(-c2ccccc2)nc1CCc1cccc(N2CCOCC2)n1]

According to the procedures described in examples 2 and 5, the title compound was prepared using 2-chloromethyl-1-methyl-4-phenyl-1H-imidazole (CAS 1201687-66-2) as starting material in the 1st step (preparation of the Wittig salt) and 6-morpholinopicolinaldehyde in the 2nd step (Wittig reaction). Colorless viscous oil.

MS: M=349.4 (M+H)+

Example 8

2,3,5-Trimethyl-6-(2-(6-(pyrrolidin-1-yl)pyridin-2-yl)ethyl)pyrazine

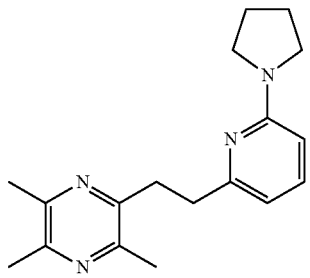 [SMILES: Cc1nc(C)c(CCc2cccc(N3CCCC3)n2)nc1C]

Step 1: 2-Chloromethyl-3,5,6-trimethyl-pyrazine hydrochloride

To a stirred, cooled (0° C.) solution of (3,5,6-trimethyl-pyrazin-2-yl)methanol (0.3 g, 1.97 mmol) in dichloromethane (5 ml) under an argon atmosphere was added dropwise a solution of thionyl chloride (469 mg, 286 μl, 3.94 mmol) in 2 ml CH₂Cl₂. When the addition was complete, the ice bath was removed and stirring at r.t. was continued for 2 hrs. The mixture was concentrated to dryness to leave the crude product as a light red solid (417 mg) which was used in the next step without further purification.

MS: M=171.1 (M+H)+

Step 2: 2,3,5-Trimethyl-6-(2-(6-(pyrrolidin-1-yl)pyridin-2-yl)ethyl)pyrazine

According to the procedures described in examples 2 and 5, the title compound was prepared using 6-(pyrrolidin-1-yl)picolinaldehyde in the 2nd step (Wittig reaction). Colorless viscous oil.

MS: M=297.6 (M+H)+

Example 9

2-Methyl-3-((6-(pyrrolidin-1-yl)pyridin-2-yl)methoxy)quinoxaline

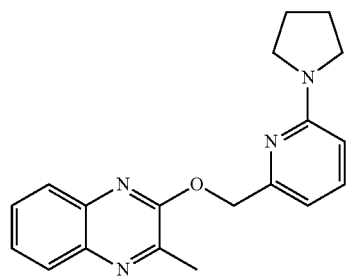 [SMILES: Cc1nc2ccccc2nc1OCc1cccc(N2CCCC2)n1]

To a suspension of NaH (33.7 mg, 842 μmol) in DMF (3 ml) at 0° under an argon atmosphere was added (6-(pyrrolidin-1-yl)pyridin-2-yl)methanol (0.1 g, 561 μmol) and 2-chloro-3-methylquinoxaline (150 mg, 842 μmol). The mixture was stirred at 0° for 2.5 hrs. At 0° water was given to the reaction mixture. The product was extracted with EtOAc, washed with water, dried over MgSO$_4$, filtered and evaporated. The crude product was purified by column chromatography using a CH$_2$Cl$_2$/MeOH gradient as eluent, providing the title compound (0.15 g, 83%) as off-white solid.

MS: M=321.1 (M+H)+

Example 10

2-Methyl-3-[(E)-2-(6-pyrrolidin-1-yl-pyridin-2-yl)-vinyl]-quinoxaline

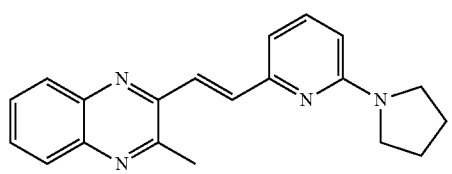 [SMILES: Cc1nc2ccccc2nc1/C=C/c1cccc(N2CCCC2)n1]

Using similar procedures as described in example 2, the title compound was prepared using 2-chloromethyl-3-methyl-quinoxaline (CAS 5559-53-5) as starting material in the 1$^{st}$ step (preparation of the Wittig salt) and 6-(pyrrolidin-1-yl)picolinaldehyde in the 2$^{nd}$ step (Wittig reaction).

MS: M 317.0 (M+H)+

Example 11

2-Methyl-3-[2-(6-pyrrolidin-1-yl-pyridin-2-yl)-ethyl]-quinoxaline

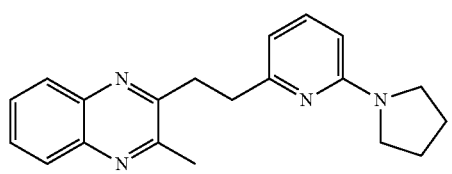 [SMILES: Cc1nc2ccccc2nc1CCc1cccc(N2CCCC2)n1]

A solution of 2-methyl-3-[(E)-2-(6-pyrrolidin-1-yl-pyridin-2-yl)-vinyl]-quinoxaline (4) (60 mg, 0.19 mmol) in methanol (20 ml) was purged with argon for 30 min, treated with Raney Nickel (40 mg; pre-washed 3× with MeOH) and stirred under a hydrogen atmosphere (balloon) for 1 h at 25° C. The reaction mixture was filtered through a celite bed, washed with methanol (30 ml). The filtrate was concentrated under reduced pressure. The crude product was purified by silica column eluting with 30% ethyl acetate in hexane to give the title compound as pale yellow solid (26.0 mg, 43%). LC-MS: 319 (M+H).

MS: M=319.4 (M+H)+

Example 12

2-[2-(5-Methyl-2-phenyl-oxazol-4-yl)-ethyl]-6-pyrrolidin-1-yl-pyridine

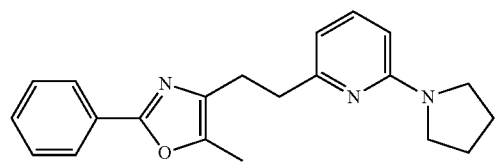 [SMILES: Cc1oc(-c2ccccc2)nc1CCc1cccc(N2CCCC2)n1]

Using similar procedures as described in examples 2 and 11, the title compound was prepared using 4-chloromethyl-5-methyl-2-phenyl-oxazole (103788-61-0) as starting material in the 1$^{st}$ step (preparation of the Wittig salt) and 6-(pyrrolidin-1-yl)-picolinaldehyde in the 2$^{nd}$ step (Wittig reaction).

MS: M 333.8 (M+H)+

Example 13

4-(6-Chloro-2-((6-(pyrrolidin-1-yl)pyridin-2-yl)methoxy)quinazolin-4-yl)morpholine

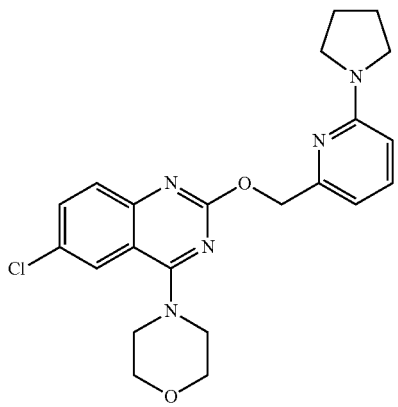 [SMILES: Clc1ccc2nc(OCc3cccc(N4CCCC4)n3)nc(N3CCOCC3)c2c1]

According to the procedure described in example 9, the title compound was prepared from 4-(2,6-dichloroquinazolin-4-yl)morpholine (CAS 39216-94-9). White solid.

MS: M=426.1 (M+H)+

Example 14

2-(2-(1-Methyl-4-phenyl-1H-imidazol-2-yl)ethyl)-6-(pyrazolidin-1-yl)pyrazine hydrochloride

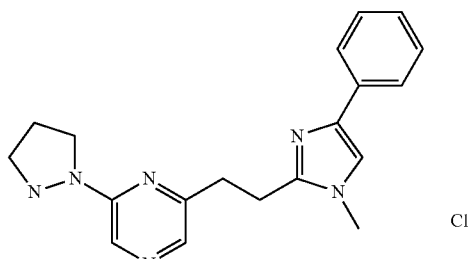

Step 1: 2-Bromo-6-(bromomethyl)pyrazine

To a solution of 2-bromo-6-methylpyrazine (3 g, 17.3 mmol) in carbon tetrachloride (30 ml) were added at r.t. under an argon atmosphere N-bromo succinimide (3.39 g, 19.1 mmol) and benzoyl peroxide (420 mg, 1.73 mmol). The mixture was stirred for 40 hr and a 75 W lamp was shining on the reaction mixture. Then, the mixture was filtered, washed with CCl$_4$ and evaporated. The residue was dissolved in EtOAc, washed with saturated aqueous NaHCO$_3$ solution, brine, dried over MgSO$_4$, filtered and evaporated. The crude product was purified by silica gel chromatography with a CH$_2$Cl$_2$/MeOH gradient as eluent, providing the title compound (1.42 g, 33%) as off-white solid.

Step 2: (E)-2-Bromo-6-(2-(1-methyl-4-phenyl-1H-imidazol-2-yl)vinyl)pyrazine

According to the procedures described in example 2, the title compound was prepared using 2-bromo-6-(bromomethyl)pyrazine as starting material in the 1$^{st}$ step (preparation of the Wittig salt) and 1-methyl-4-phenyl-1H-imidazole-2-carb-aldehyde (CAS 123511-51-3) in the 2$^{nd}$ step (Wittig reaction). Yellow solid.
MS: M=341.1 (M+H)+

Step 3: (E)-tert-butyl 2-(6-(2-(1-methyl-4-phenyl-1H-imidazol-2-yl)vinyl)pyrazin-2-yl)pyrazolidine-1-carboxylate A mixture of tert-butyl pyrazolidine-1-carboxylate (60 mg, 348 µmol), (E)-2-bromo-6-(2-(1-methyl-4-phenyl-1H-imidazol-2-yl)vinyl)pyrazine (166 mg, 488 µmol), water (13.2 mg, 13.2 µl, 732 µmol) and potassium carbonate (86.7 mg, 627 µmol) were mixed together at r.t. in xylene (5 ml). Degassing by applying vacuum followed by argon filling was repeated 3 times. Palladium (II) acetate (3.13 mg, 13.9 µmol) was added, then the vacuum/argon filling procedure was repeated. Xantphos (10.1 mg, 17.4 µmol) was added, followed again by the vacuum/argon filling procedure. The mixture was heated to 140° C. overnight, then cooled to r.t., diluted with CH$_2$Cl$_2$ and stirred for 5 min at r.t. The solids were filtered off and washed with CH$_2$Cl$_2$. The filtrate was concentrated. The crude product was purified by silica gel chromatography with a CH$_2$Cl$_2$/MeOH gradient as eluent, providing the title compound (44 mg, 80% purity, 23%) as orange solid.
MS: M=433.1 (M+H)+

Step 4: tert-Butyl 2-(6-(2-(1-methyl-4-phenyl-1H-imidazol-2-yl)ethyl)pyrazin-2-yl)-pyrazolidine-1-carboxylate According to the procedure described in example 5, the title compound was obtained as off-white solid.
MS: M=435.1 (M+H)+

Step 5: 2-(2-(1-Methyl-4-phenyl-1H-imidazol-2-yl)ethyl)-6-(pyrazolidin-1-yl)pyrazine hydrochloride To a solution of tert-butyl 2-(6-(2-(1-methyl-4-phenyl-1H-imidazol-2-yl)ethyl)pyrazin-2-yl)pyrazolidine-1-carboxylate (0.021 g, 48.3 µmol) in methanol (1 ml) was added at 0° C. and under an argon atmosphere 4M HCl in dioxane (242 µl, 967 µmol). The mixture was stirred at r.t overnight, then evaporated to dryness 10 give the title compound (19 mg, 95%) as off-white solid.
MS: M=335.1 (M+H)+

Example 15

2-Methyl-3-((6-(piperidin-1-yl)pyridin-2-yl)methoxy)quinoxaline

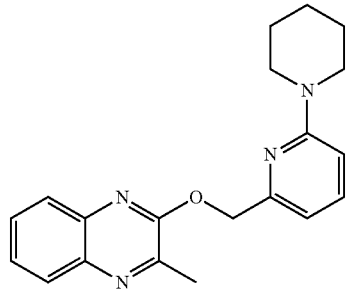 [SMILES: Cc1nc2ccccc2nc1OCc1cccc(N2CCCCC2)n1]

According to the procedure described in example 9, the title compound was obtained from 2-chloro-3-methylquinoxaline and (6-(piperidin-1-yl)pyridin-2-yl)methanol. Off-white solid.
MS: M=335.0 (M+H)+

Example 16

4-(2-((6-(Pyrrolidin-1-yl)pyridin-2-yl)methoxy)quinazolin-4-yl)morpholine

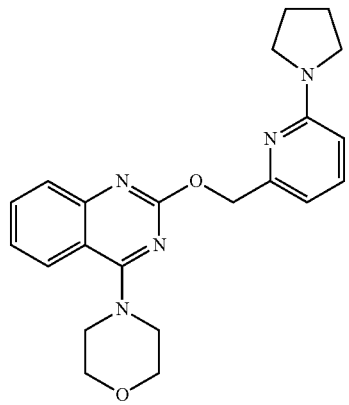 [SMILES: c1cc(COc2nc(N3CCOCC3)c3ccccc3n2)nc(N2CCCC2)c1]

According to the procedure described in example 9, the title compound was obtained from (6-(pyrrolidin-1-yl)pyridin-2-yl)methanol and 4-(2-chloroquinazolin-4-yl)-morpholine. Colorless amorphous solid.
MS: M=392.2 (M+H)+

Example 17

6-Chloro-N,N-dimethyl-2-((6-(pyrrolidin-1-yl)pyridin-2-yl)methoxy)quinazolin-4-amine

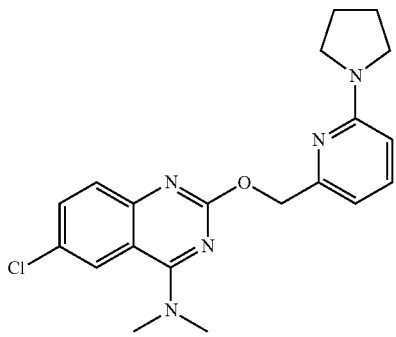 [SMILES: CN(C)c1nc(OCc2cccc(N3CCCC3)n2)nc2ccc(Cl)cc12]

Step 1: (2,6-Dichloro-quinazolin-4-yl)-dimethyl-amine

To a solution of 2,4,6-trichloroquinazoline (497 mg, 2.08 mmol) in CHCl$_3$ (15 ml) was added dimethylamine hydrochloride (177.3 mg, 2.17 mmol), followed by the addition of triethylamine (436 mg, 0.6 mL, 4.31 mmol). The reaction mixture was stirred at r.t. over night. The reaction mixture was quenched with water. Organic and aqueous layers were separated. The organic layer was washed well with water, then with brine, dried over anhydrous MgSO$_4$ and filtered. The crude product (512 mg, quantitative) was used for the next step without further purification.
MS: M (M+H)=242.1

Step 2: 6-Chloro-N,N-dimethyl-2-((6-(pyrrolidin-1-yl)pyridin-2-yl)methoxy)quinazolin-4-amine According to the procedure described in example 9, the title compound was obtained from (2,6-dichloro-quinazolin-4-yl)-dimethyl-amine and (6-(pyrrolidin-1-yl)pyridin-2-yl)methanol. Yellow solid.
MS: M=384.0 (M+H)+

Example 18

4-(1-Methyl-6-(((6-(pyrrolidin-1-yl)pyridin-2-yl)methoxy)-1H-pyrazolo-[3,4-d]pyrimidin-4-yl)morpholine

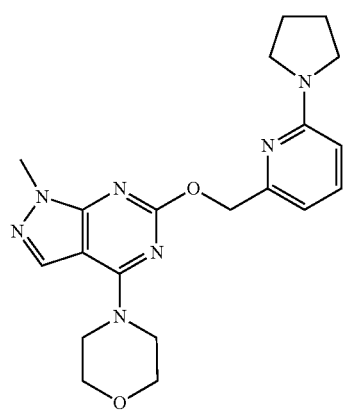 [SMILES: Cn1ncc2c(N3CCOCC3)nc(OCc3cccc(N4CCCC4)n3)nc21]

According to the procedure described in example 9, the title compound was obtained from (6-(pyrrolidin-1-yl)pyridin-2-yl)methanol and 4-(6-chloro-1-methyl-1H-pyrazolo-[3,4-d]pyrimidin-4-yl)morpholine. White solid.
MS: M=396.1 (M+H)+

Example 19

(E)-4-(6-Chloro-2-(2-(6-(pyrrolidin-1-yl)pyridin-2-yl)vinyl)quinazolin-4-yl)morpholine

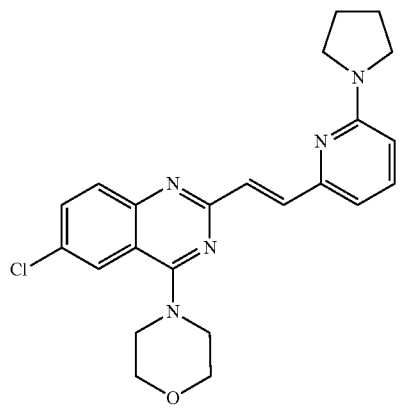 [SMILES: Clc1ccc2nc(/C=C/c3cccc(N4CCCC4)n3)nc(N3CCOCC3)c2c1]

Step 1: 4,6-Dichloro-2-(chloromethyl)quinazoline

A weak stream of dry HCl gas was bubbled into a cooled (between 0° C. and 5° C.) solution of 2-amino-5-chlorobenzonitrile (4.416 g, 28.9 mmol) and 2-chloroacetonitrile (5.09 g, 4.28 ml, 67.4 mmol) in dioxane (150 ml) for 7 h (note: after a few minutes, the mixture turned to yellow and a solid started to precipitate out; after ~1 hr the yellow color had disappeared and the precipitate had turned light brown; after ~5 h, the mixture had turned to a clear orange solution). The bubbling was stopped after 7 hrs and the mixture was stirred at r.t. overnight, then purged with argon and concentrated. The crude product was taken up in H$_2$O/EtOAc. The organic phase was washed with brine, dried (MgSO$_4$), filtered and concentrated. The crude product was purified by silica gel chromatography with a n-heptane/EtOAc gradient as eluent. The product-containing fractions were concentrated. The residue was taken up in cyclohexane (25 ml) and triturated for 2 hrs. The product was collected by filtration, washed with cyclohexane and dried to give a off-white crystalline solid (5.32 g, 74%).
MS: M=246.0 (M)

Step 2: 4-(6-Chloro-2-(chloromethyl)quinazolin-4-yl)morpholine

To a stirred mixture of 4,6-dichloro-2-(chloromethyl)quinazoline (500 mg, 2.0 mmol) and morpholine (176 mg, 176 μl, 2.0 mmol) at r.t. in THF under an argon atmosphere was added triethylamine (245 mg, 336 μl, 2.4 mmol). The mixture was stirred at r.t. for 2 hrs. The mixture was diluted with EtOAc and 10% Na$_2$CO$_3$. The layers were separated and the aqueous phase was back extracted with EtOAc. The combined organics were washed H$_2$O and brine, dried over MgSO$_4$, filtered and concentrated to leave the crude product as a light brown syrup. The crude product was purified by silica gel chromatography using a n-heptane/EtOAc gradient as eluent, providing the title compound (390 mg, 65%) as off-white solid.

MS: M=298.0 (M+H)+

Step 3: (E)-4-(6-chloro-2-(2-(6-(pyrrolidin-1-yl)pyridin-2-yl)vinyl)quinazolin-4-yl)morpholine According to the procedures described in example 2, the title compound was obtained using 6-(pyrrolidin-1-yl)picolinaldehyde in the 2nd step (Wittig reaction). Yellow solid.

MS: M=421.9 (M+H)+

Example 20

4-(6-Chloro-2-(2-(6-(pyrrolidin-1-yl)pyridin-2-yl)ethyl)quinazolin-4-yl)morpholine

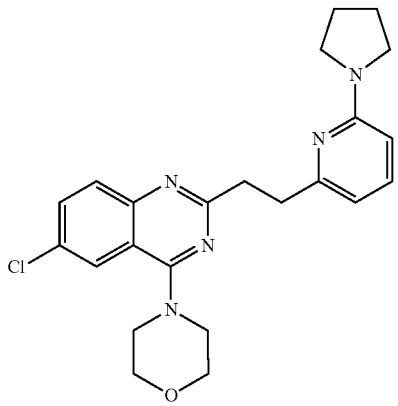 [SMILES: Clc1ccc2nc(CCc3cccc(N4CCCC4)n3)nc(N3CCOCC3)c2c1]

According to the procedure described in example 11, the title compound was obtained from (E)-4-(6-chloro-2-(2-(6-(pyrrolidin-1-yl)pyridin-2-yl)vinyl)quinazolin-4-yl)morpholine. Light brown viscous oil.

MS: M=424.0 (M+H)+

Example 21

4-(2-(2-(6-(Pyrrolidin-1-yl)pyridin-2-yl)ethyl)quinazolin-4-yl)morpholine

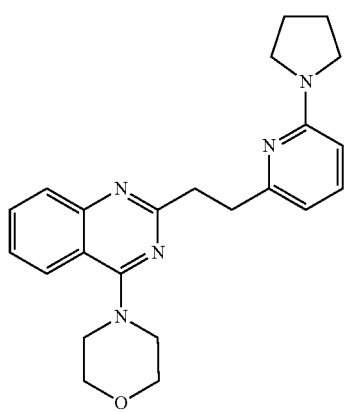 [SMILES: c1cc(CCc2nc(N3CCOCC3)c3ccccc3n2)nc(N2CCCC2)c1]

The title compound was obtained as side product from the reaction described in example 20. Light brown viscous oil.

MS: M=390.0 (M+H)+

Example 22

6-Chloro-2-((6-(pyrrolidin-1-yl)pyridin-2-yl)methoxy)-4-(tetrahydro-2H-pyran-4-yloxy)quinazoline

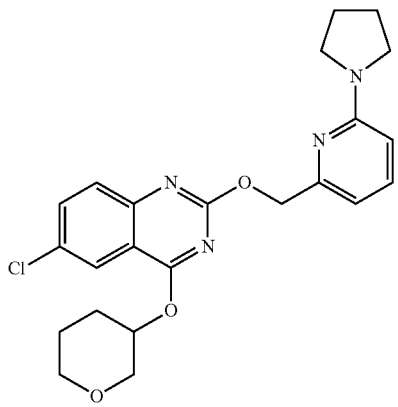 [SMILES: Clc1ccc2nc(OCc3cccc(N4CCCC4)n3)nc(OC3CCCOC3)c2c1]

Step 1: 2,6-Dichloro-4-(tetrahydro-2H-pyran-4-yloxy)quinazoline

To a stirred suspension of sodium hydride 60% suspension in mineral oil (86.5 mg, 2.16 mmol) at 0° C. in DMF (10 ml) under an Argon atmosphere was added tetrahydro-2H-pyran-4-ol (214 mg, 0.20 ml, 2.1 mmol). After 5 min stirring, 2,4,6-trichloroquinazoline (501.1 mg, 2.15 mmol) was added in one portion and stirring at 0° C. was continued for 10 min. The ice bath was removed and stirring at r.t. was continued for 5 hrs. The reaction mixture was diluted with AcOEt and washed with water. The aqueous phase was back-extracted with AcOEt. The combined organic phases were washed with brine, dried over anhydrous MgSO$_4$, filtered and concentrated in vacuo. The crude product was purified by silica gel chromatography using a n-heptane/EtOAc gradient as eluent, to provide the title compound (481 mg, 75%) as light yellow solid.

Step 2: 6-Chloro-2-((6-(pyrrolidin-1-yl)pyridin-2-yl)methoxy)-4-(tetrahydro-2H-pyran-4-yloxy)quinazoline According to the procedure described in example 9, the title compound was obtained by reacting 2,6-dichloro-4-(tetrahydro-2H-pyran-4-yloxy)quinazoline with (6-(pyrrolidin-1-yl)pyridin-2-yl)methanol. Light yellow solid.

MS: M=440.9 (M+H)+

Example 23

4-[2-(2H-Pyrazol-3-yl)-6-(6-pyrrolidin-1-yl-pyridin-2-ylmethoxy)-pyrimidin-4-yl]-morpholine

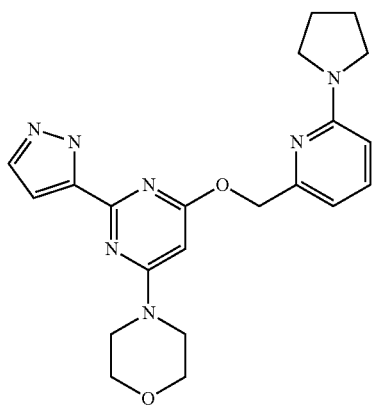 [SMILES: c1cc(COc2cc(N3CCOCC3)nc(-c3ccn[nH]3)n2)nc(N2CCCC2)c1]

Step 1: 4-(2-Chloro-6-((6-(pyrrolidin-1-yl)pyridin-2-yl)methoxy)pyrimidin-4-yl)-morpholine According to the procedures described in example 17, the title compound was obtained by reacting 2,4,6-trichloropyrimidine and morpholine in the 1st step and using (6-(pyrrolidin-1-yl)pyridin-2-yl)methanol in the 2nd step.

MS: M=376.1 (M+H)+

Step 2: 4-[2-(2H-Pyrazol-3-yl)-6-(6-pyrrolidin-1-yl-pyridin-2-ylmethoxy)-pyrimidin-4-yl]-morpholine To 4-(2-chloro-6-((1-methyl-4-phenyl-1H-imidazol-2-yl)methoxy)pyrimidin-4-yl)morpholine (0.09 g, 233 µmol) in 1,2-dimethoxyethane (8 ml) were added 3-(4,4,5,5-tetramethyl-1,3,2-dioxaborolan-2-yl)-1H-pyrazole (155 mg, 7.98 µmol) sodium carbonate 2 M (233 µl, 467 µmol) and tetrakis(triphenylphosphine)palladium(0) (8.09 mg, 7.00 µmol). The mixture was refluxed overnight. After cooling to r.t., the mixture was evaporated. The residue was diluted with AcOEt, washed with water, dried over MgSO₄, filtered and evaporated. The crude product was purified by silica gel chromatography using a CH₂Cl₂/MeOH gradient as eluent. The product-containing fractions were combined and concentrated. The residue was triturated in diethyl ether, filtered and dried to provide the tile compound (29 mg, 13%) as white solid.

MS: M=408.4 (M+H)+

Example 24

4-(2-(Pyridin-3-yl)-6-((6-(pyrrolidin-1-yl)pyridin-2-yl)methoxy)-pyrimidin-4-yl)morpholine

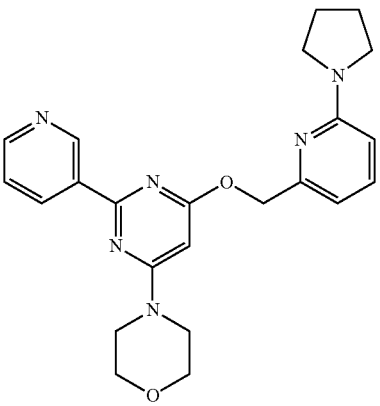 [SMILES: c1cncc(-c2nc(OCc3cccc(N4CCCC4)n3)cc(N3CCOCC3)n2)c1]

According to the procedure described in example 23, step 2, the title compound was obtained from 4-(2-chloro-6-((1-methyl-4-phenyl-1H-imidazol-2-yl)methoxy)pyrimi-din-4-yl)morpholine and 3-(4,4,5,5-tetramethyl-1,3,2-dioxaborolan-2-yl)pyridine. White solid.

MS: M=419.1 (M+H)+

Example 25

(E)-(1-(6-(2-(6-Chloro-4-(dimethylamino)quinazolin-2-yl)vinyl)pyridin-2-yl)pyrrolidin-3-yl)methanol

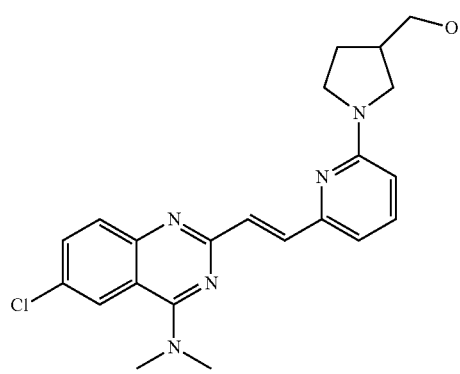 [SMILES: CN(C)c1nc(/C=C/c2cccc(N3CCC(CO)C3)n2)nc2ccc(Cl)cc12]

Step 1: (E)-2-(2-(6-Bromopyridin-2-yl)vinyl)-6-chloro-N,N-dimethylquinazolin-4-amine According to the procedures described in example 19(step 2 and 3), 4,6-dichloro-2-(chloromethyl)quinazoline was reacted with dimethylamine hydrochloride in the 1st step and then converted to the title compound using 6-bromo-2-pyridinecarbaldehyde in the 3rd step (Wittig reaction). Light yellow solid.

MS: M=391.0 (M+H)+

Step 2: (E) (1 (6 (2 (6 Chloro-4-(dimethylamino) quinazolin-2-yl)vinyl)pyridin-2-yl)pyrrolidin-3-yl) methanol A mixture of (E)-2-(2-(6-bromopyridin-2-yl)vinyl)-6-chloro-N,N-dimethylquinazolin-4-amine (0.2 g, 513 µmol), pyrrolidin-3-ylmethanol (51.9 mg, 513 µmol), potassium carbonate (128 mg, 924 µmol) and water (19.4 mg, 19.4 µl, 1.08 mmol) in xylene (3 ml) was evacuated and then flushed by argon 3 times. Palladium(II) acetate (4.61 mg, 20.5 µmol) was added and again, the reaction mixture was evacuated followed by argon flushing. Xantphos (14.8 mg, 25.7 µmol) was added, followed by evacuation and argon flushing. The mixture was heated to 140° C. and stirring at that temperature was continued overnight. The mixture was cooled to r.t., diluted with $CH_2Cl_2$ and stirred for 5 min at r.t. The solids were filtered off and washed with $CH_2Cl_2$. The filtrate was concentrated. The crude product was purified by silica gel chromatography using a $CH_2Cl_2$/MeOH gradient as eluent, providing the title compound (35 mg, 17%) as yellow solid.
MS: M=410.2 (M+H)+

Example 26

5-Chloro-2-(2-(6-(pyrrolidin-1-yl)pyridin-2-yl)ethyl) quinazolin-4(3H)-one

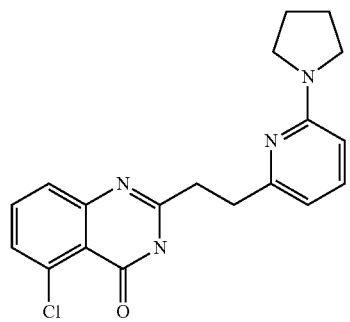 [SMILES: O=c1[nH]c(CCc2cccc(N3CCCC3)n2)nc2cccc(Cl)c12]

Step 1:
5-Chloro-2-(chloromethyl)quinazolin-4(3H)-one

To a solution of sodium methoxide in methanol (5.4 M, 540 µl, 2.91 mmol) were added MeOH (10 ml) and 2-chloroacetonitrile (1.01 g, 848 µl, 13.4 mmol) at r.t. under an argon atmosphere. The mixture was stirred at r.t. for 30 min. A solution of 2-amino-6-chlorobenzoic acid (2 g, 11.7 mmol) in methanol (50.0 ml) was then added dropwise at r.t. The clear brown solution was stirred at r.t. for 2 hrs. A solid started to precipitate out after ca. 90 min. The flask was placed in an oil bath preheated to 80° C. and the mixture was stirred at 80° C. for 2 hrs, turning back to a clear light brown solution after a few minutes. The mixture was cooled to r.t., and a solid started to precipitate out. The suspension was stirred at r.t. overnight. The solid was collected by filtration, washed with MeOH (15 ml), $H_2O$ (15 ml) and dried to provide a first crop of the title compound (840 mg). Grey powder.

The filtrate was concentrated to leave a brown sticky solid. The crude product was purified by silica gel chromatography using a $CH_2Cl_2$/MeOH gradient as eluent. The product-containing fractions were combined and concentration. The residue was triturated in $CH_2Cl_2$, filtered and dried to provide a second crop of the title compound (800 mg). Off-white solid. Total yield: 1.64 g (62%).
MS: M=228.9 (M+H)+

Step 2: (E)-5-chloro-2-(2-(6-(pyrrolidin-1-yl)pyridin-2-yl)vinyl)quinazolin-4(3H)-one According to the procedures described in example 2, 5-chloro-2-(chloromethyl)-quinazolin-4(3H)-one was converted to the title compound, using 6-(pyrrolidin-1-yl)-picolinaldehyde in the 2nd step (Wittig reaction). Yellow solid.
MS: M=353.3 (M+H)+

Step 3: 5-Chloro-2-(2-(6-(pyrrolidin-1-yl)pyridin-2-yl)ethyl)quinazolin-4(3H)-one According to the procedure described in example 11, (E)-5-chloro-2-(2-(6-(pyrrolidin-1-yl)pyridin-2-yl)vinyl) quinazolin-4(3H)-one was converted to the title compound. Yellow solid.
MS: M=355.1 (M+H)+

Example 27

6-Chloro-5-methoxy-2-(2-(6-(pyrrolidin-1-yl)pyridin-2-yl)ethyl)-quinazolin-4(3H)-one

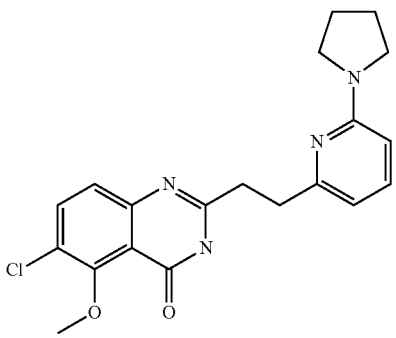 [SMILES: COc1c(Cl)ccc2nc(CCc3cccc(N4CCCC4)n3)[nH]c(=O)c12]

Step 1: 6-Chloro-2-(chloromethyl)-5-methoxyquinazolin-4-amine

A weak stream of dry HCl gas was bubbled into a cooled (between 0° C. and 5° C.) solution of 6-amino-3-chloro-2-methoxybenzonitrile (3 g, 16.4 mmol, prepared from 3-chloro-2-methoxy-6-nitro-benzonitrile (CAS 89892-61-5) by hydrogenation in the presence of Pd/C and HCl in THF) and 2-chloroacetonitrile (2.89 g, 2.43 ml, 38.3 mmol) in dioxane (100 ml) for 7 hrs. After a few minutes, the mixture turned to orange and a solid started to precipitate out. After 5 hrs the mixture had turned to a clear orange solution. The bubbling was stopped after 7 hrs, and the mixture was stirred at r.t. for another 16 hrs, purged with argon and then concentrated. The orange oil was taken up in $H_2O$. The precipitate was filtered, washed with water and dried to give 4,6-dichloro-2-(chloromethyl)-5-methoxyquinazoline (0.82 g, 16%) as side product. Off-white solid.
MS: M=278.8 (M+H)+

The aqueous filtrate phase was basified with 4N NaOH. The resulting precipitate was filtered, washed with water and dried to give the title compound (3.5 g, 83%) as light grey solid.
MS: M=259.9 (M+H)+

Step 2: 6-Chloro-2-chloromethyl-5-methoxy-3H-quinazolin-4-one

A suspension of 6-chloro-2-(chloromethyl)-5-methoxy-quinazolin-4-amine (2.07 g, 8.02 mmol) in 6 N HCl (50 ml) was heated to 95° C. The mixture soon turned to a clear brown/orange solution) and stirring at that temperature was continued overnight. A solid had precipitated out. The mixture was cooled to r.t., the solid was collected by filtration, washed with H₂O and cyclohexane and dried. The crude product (1.4 g, not very pure) was used in the next reaction step without further purification.
MS: M=258.9 (M+H)+

Step 3: 6-Chloro-5-methoxy-2-(2-(6-(pyrrolidin-1-yl)pyridin-2-yl)ethyl)-quinazolin-4(3H)-one In analogy to the procedures described in example 2 and 11, 6-chloro-2-chloromethyl-5-methoxy-3H-quinazolin-4-one was converted to the tile compound. Off-white solid.
MS: M=385.1 (M+H)+

Example 28

7,8-Dimethyl-2-(2-(6-(pyrrolidin-1-yl)pyridin-2-yl)ethyl)-1H-purin-6(7H)-one

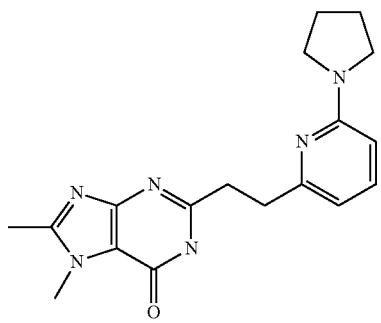 [SMILES: Cc1nc2nc(CCc3cccc(N4CCCC4)n3)[nH]c(=O)c2n1C]

Step 1:
2-(Chloromethyl)-7,8-dimethyl-7H-purin-6-amine

Using a method similar to the procedure described in example 27, step 1, the title compound was obtained from 5-amino-2,3-dimethyl-3H-imidazole-4-carbonitrile (CAS 58192-81-7).
MS: M=211.9 (M+H)+

Step 2: 2-(Chloromethyl)-7,8-dimethyl-1H-purin-6(7H)-one

To a stirred solution of 2-(chloromethyl)-7,8-dimethyl-7H-purin-6-amine (1.5 g, 7.09 mmol) at r.t. in acetic acid (45.0 ml) under an argon atmosphere was added dropwise sodium nitrite 0.73 M in H₂O (34.0 ml, 24.8 mmol) for 30 min. When the addition was complete, the mixture was heated to 65° C. and stirring at that temperature was continued overnight. The mixture was cooled to r.t. and concentrated to leave the crude product as a light yellow solid. This was carefully treated with 10% KHCO₃ until pH~6 was reached. The solid was collected by filtration, washed with H₂O and dried to provide the title compound (717 mg) as an off-white solid. The filtrate was concentrated to leave a solid.

This was taken up in H₂O and extracted with CH₂Cl₂/MeOH 9:1. The aqueous phase was back extracted with CH₂Cl₂/MeOH 9:1. The combined organics were washed with brine, dried over MgSO₄, filtered and concentrated to leave a small amount of a light yellow solid which was combined to the previous collected solid. This was triturated in 5 ml MeOH. The product was collected by filtration, washed with some MeOH and dried to give the title compound (685 mg, 46%) as light yellow solid.
MS: M=212.9 (M+H)+

Step 3: 7,8-Dimethyl-2-(2-(6-(pyrrolidin-1-yl)pyridin-2-yl)ethyl)-1H-purin-6(7H)-one According to the procedures described in examples 2 and 5, the title compound was prepared using 6-(pyrrolidin-1-yl)picolinaldehyde in the 2nd step (Wittig reaction). White solid.
MS: M=339.4 (M+H)+

Example 29

6-Chloro-2-(2-(6-(pyrrolidin-1-yl)pyridin-2-yl)ethyl)quinazolin-4(3H)-one

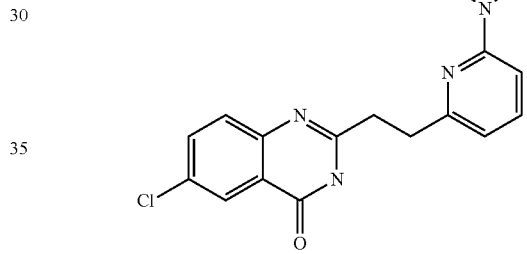

According to the procedures described in example 26, the title compound was obtained from 2-amino-5-chlorobenzoic acid and using 6-(pyrrolidin-1-yl)picolinaldehyde in the Wittig reaction. Off-white solid.
MS: M=355.1 (M+H)+

Example 30

2-(2-(6-(2,5-Dimethylpyrrolidin-1-yl)pyridin-2-yl)ethyl)-N,N-dimethylquinazolin-4-amine

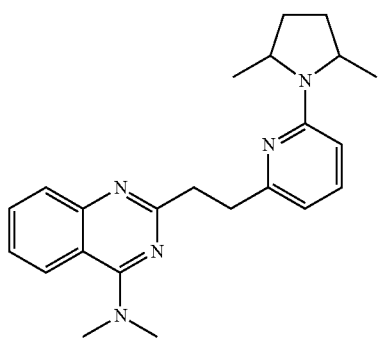 [SMILES: CC1CCC(C)N1c1cccc(CCc2nc(N(C)C)c3ccccc3n2)n1]

Step 1: (E)-6-chloro-2-(2-(6-(2,5-dimethylpyrrolidin-1-yl)pyridin-2-yl)vinyl)-N,N-dimethylquinazolin-4-amine According to the procedure described in step 2 of example 25, the title compound was obtained by reacting (E)-2-(2-(6-bromopyridin-2-yl)vinyl)-6-chloro-N,N-dimethyl-quinazolin-4-amine with 2,5-dimethylpyrrolidine. Yellow solid.
MS: M=408.3 (M+H)+

Step 2: 2-(2-(6-(2,5-Dimethylpyrrolidin-1-yl)pyridin-2-yl)ethyl)-N,N-dimethylquinazolin-4-amine The title compound was obtained according to the procedure described in example 11. Light yellow gum.
MS: M=376.1 (M+H)+

Example 31

1-(6-(2-(6-Chloro-4-(dimethylamino)quinazolin-2-yl)ethyl)pyridin-2-yl)pyrrolidin-3-ol

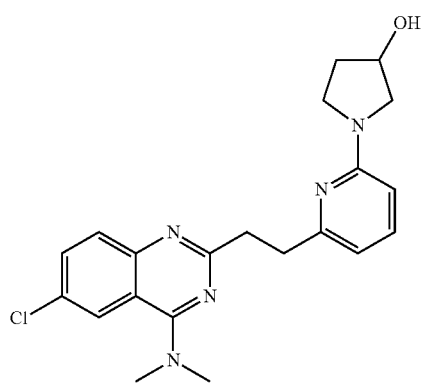 [SMILES: CN(C)c1nc(CCc2cccc(N3CCC(O)C3)n2)nc2ccc(Cl)cc12]

The title compound was obtained according to the procedures described in example 30, using 3-hydroxy-pyrolidine in the 1st step. Yellow solid.
MS: M=398.0 (M+H)+

Example 32

1-(6-(2-(4-(Dimethylamino)quinazolin-2-yl)ethyl)pyridin-2-yl)-pyrrolidin-3-ol

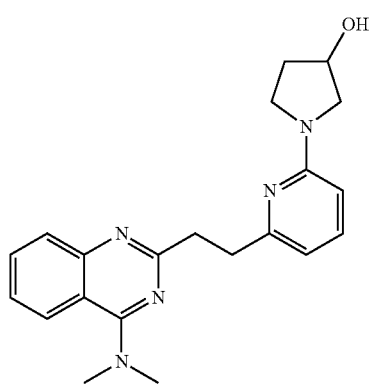 [SMILES: CN(C)c1nc(CCc2cccc(N3CCC(O)C3)n2)nc2ccccc12]

The title compound was obtained as a side product in the final step of the preparation of 1-(6-(2-(6-chloro-4-(dimethylamino)quinazolin-2-yl)ethyl)pyridin-2-yl)-pyrrolidin-3-ol (example 31). Yellow gum.
MS: M=364.3 (M+H)+

Example 33

(1-(6-(2-(6-Chloro-4-(dimethylamino)quinazolin-2-yl)ethyl)pyridin-2-yl)pyrrolidin-3-yl)methanol

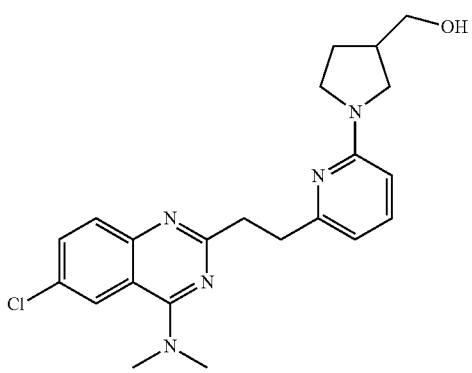 [SMILES: CN(C)c1nc(CCc2cccc(N3CCC(CO)C3)n2)nc2ccc(Cl)cc12]

The title compound was obtained according to the procedures described in example 30, using 3-hydroxymethyl-pyrolidine in the 1st step and Pd/C 10% as hydrogenation catalyst in the 2nd step. Yellow gum.
MS: M=412.1 (M+H)+

Example 34

(1-(6-(2-(4-(Dimethylamino)quinazolin-2-yl)ethyl)pyridin-2-yl)pyrrolidin-3-yl)methanol

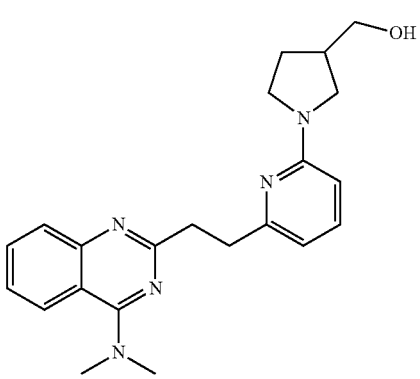 [SMILES: CN(C)c1nc(CCc2cccc(N3CCC(CO)C3)n2)nc2ccccc12]

The title compound was obtained as a side product in the final step of the preparation of (1-(6-(2-(6-chloro-4-(dimethylamino)quinazolin-2-yl)ethyl)pyridin-2-yl)pyrrolidin-3-yl)methanol (example 33). Yellow gum.
MS: M=378.1 (M+H)+

Example 35

(E)-6-Chloro-N,N-dimethyl-2-(2-(6-(2-methylpyrrolidin-1-yl)pyridin-2-yl)vinyl)quinazolin-4-amine

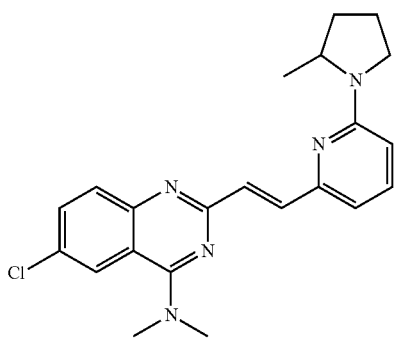 [SMILES: CC1CCCN1c1cccc(/C=C/c2nc(N(C)C)c3cc(Cl)ccc3n2)n1]

The title compound was obtained according to the procedures described in step 2 of example 25, reacting 2-methylpyrolidine and (E)-2-(2-(6-bromopyridin-2-yl)vinyl)-6-chloro-N,N-dimethylquinazolin-4-amine. Yellow solid.

MS: M=394.1 (M+H)+

Example 36

(E)-1-(6-(2-(6-chloro-4-(dimethylamino)quinazolin-2-yl)vinyl)pyridin-2-yl)pyrrolidin-2-one

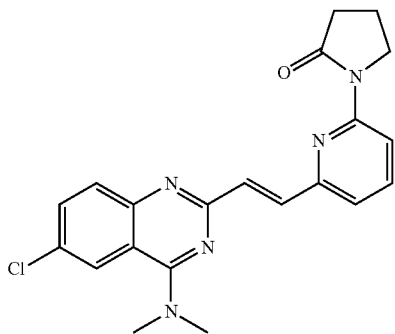 [SMILES: CN(C)c1nc(/C=C/c2cccc(N3CCCC3=O)n2)nc2ccc(Cl)cc12]

The title compound was prepared according to the procedure described in step 2 of example 25, reacting reacting pyrolidine-2-one and (E)-2-(2-(6-bromopyridin2-yl)vinyl)-6-chloro-N,N-dimethylquinazolin-4-amine

MS: M=394.4 (M+H)+

Example 37

8-methyl-2-(2-(6-(pyrrolidin-1-yl)pyridin-2-yl)ethyl)quinazolin-4(3H)-one

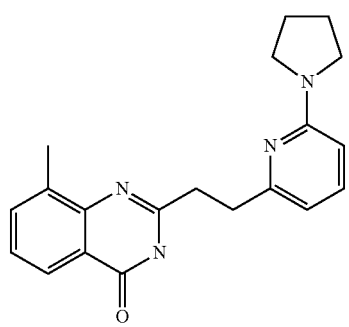 [SMILES: Cc1cccc2c(=O)[nH]c(CCc3cccc(N4CCCC4)n3)nc12]

According to the procedures described in example 26, the title compound was prepared starting from 2-amino-3-methylbenzoic acid. Off-white solid.

MS: M=335.3 (M+H)+

Example 38

6-Chloro-N,N-dimethyl-2-(2-(6-(2-methylpyrrolidin-1-yl)pyridin-2-yl)ethyl)quinazolin-4-amine

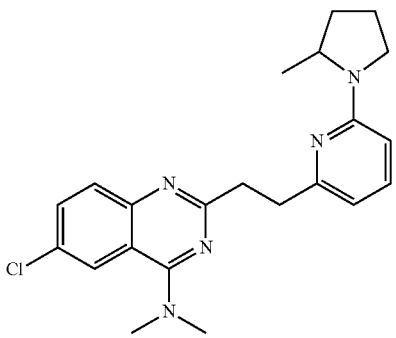 [SMILES: CC1CCCN1c1cccc(CCc2nc(N(C)C)c3cc(Cl)ccc3n2)n1]

According to the procedure described in example 5, the title compound was obtained from (E)-6-chloro-N,N-dimethyl-2-(2-(6-(2-methylpyrrolidin-1-yl)pyridin-2-yl)vinyl)-quinazolin-4-amine (example 35). Yellow gum.

MS: M=396.0 (M+H)+

Example 39

(E)-2-((6-(2-(6-Chloro-4-(dimethylamino)quinazolin-2-yl)vinyl)pyridin-2-yl)(methyl)amino)ethanol

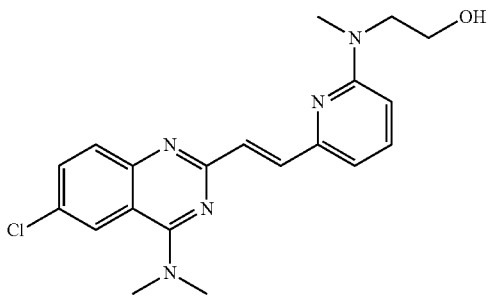 [SMILES: CN(C)c1nc(/C=C/c2cccc(N(C)CCO)n2)nc2ccc(Cl)cc12]

To a solution of (0.1 g, 257 μmol) in DMF (3 ml) was added at r.t. under an argon atmosphere 2-(methylamino)ethanol (19.3 mg, 20.5 μl, 257 μmol) and N-ethyldiisopropylamine (182 mg, 240 μl, 1.41 mmol). The mixture was stirred at 120° for 17 hr. After cooling to r.t, the mixture was dissolved in AcOEt, washed 3× with water, dried over MgSO$_4$, filtered and concentrated. The crude product was purified by silica gel chromatography using a heptane/EtOAc gradient as eluent, providing the title compound (25 mg, 25%) as yellow solid.

MS: M=384.1 (M+H)+

Example 40

2-((6-(2-(6-Chloro-4-(dimethylamino)quinazolin-2-yl)ethyl)pyridin-2-yl)(methyl)amino)ethanol

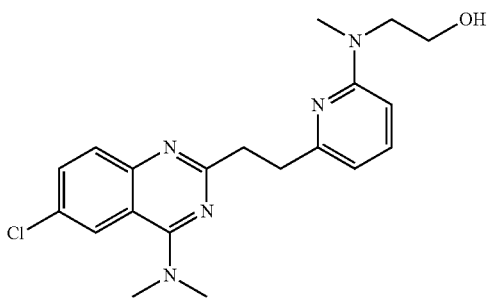 [SMILES: CN(C)c1nc(CCc2cccc(N(C)CCO)n2)nc2ccc(Cl)cc12]

The title compound was obtained from (E)-2-((6-(2-(6-chloro-4-(dimethylamino)-quinazolin-2-yl)vinyl)pyridin-2-yl)(methyl)amino)ethanol according to the procedure described in example 5. Yellow gum.

MS: M=386.0 (M+H)+

Example 41

(E)-6-Chloro-2-(2-(6-(dimethylamino)pyridin-2-yl)vinyl)-N,N-dimethylquinazolin-4-amine

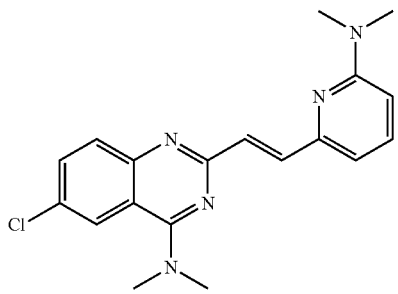 [SMILES: CN(C)c1cccc(/C=C/c2nc(N(C)C)c3cc(Cl)ccc3n2)n1]

The title compound was obtained from reacting (E)-2-(2-(6-bromopyridin-2-yl)vinyl)-6-chloro-N,N-dimethyl-quinazolin-4-amine with dimethylamine hydrochloride according to the procedure described in example 39. Yellow solid.

MS: M=354.1 (M+H)+

Example 42

6-Chloro-2-(2-(6-(dimethylamino)pyridin-2-yl)ethyl)-N,N-dimethyl-quinazolin-4-amine

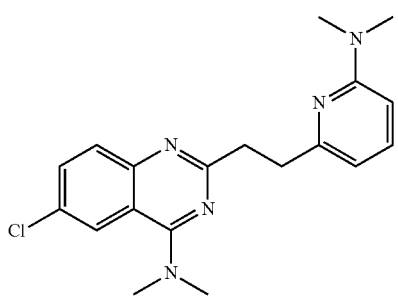 [SMILES: CN(C)c1cccc(CCc2nc(N(C)C)c3cc(Cl)ccc3n2)n1]

The title compound was obtained from (E)-6-chloro-2-(2-(6-(dimethylamino)pyridin-2-yl)vinyl)-N,N-dimethylquinazolin-4-amine according to the procedure described in example 5. Light yellow solid.

MS: M=356.3 (M+H)+

Example 43

(E)-5,8-Dimethyl-2-(2-(6-(pyrrolidin-1-yl)pyridin-2-yl)vinyl)[1,2,4]triazolo[1,5-a]pyrazine

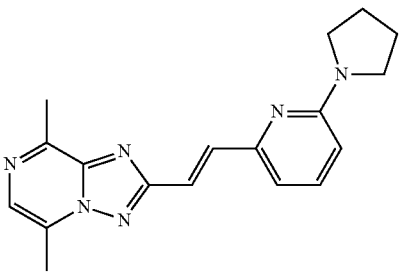 [SMILES: Cc1ncc(C)n2nc(/C=C/c3cccc(N4CCCC4)n3)nc12]

According to the procedure described in step 2 of example 2, the title compound was obtained from ((5,8-dimethyl-[1,2,4]triazolo[1,5-a]pyrazin-2-yl)methyl)triphenyl-phosphonium chloride (CAS 1201689-16-8) and 6-(pyrrolidin-1-yl)picolinaldehyde. Yellow solid.

MS: M=321.0 (M+H)+

Example 44

2,3-Dimethyl-6-((6-(pyrrolidin-1-yl)pyridin-2-yl)methoxy)imidazo[1,2-b]pyridazine

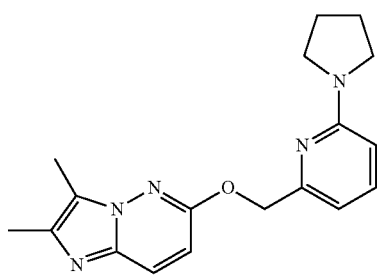 [SMILES: Cc1nc2ccc(OCc3cccc(N4CCCC4)n3)nn2c1C]

Step 1:
6-Chloro-2,3-dimethylimidazo[1,2-b]pyridazine

A mixture (clear light brown solution) of 6-chloropyridazin-3-amine (500 mg, 3.86 mmol) and 3-bromobutan-2-one (758 mg, 5.02 mmol) in EtOH (10 ml) under an argon atmosphere was heated to reflux and stirring was continued for overnight. The mixture was concentrated and the residue was taken up in 20 ml 10% KHCO₃. The precipitated solid was collected by filtration, washed with H₂O and dried to provide the title compound (392 mg 56%) as off-white solid.

MS: M=182.1 (M+H)+

Step 2: 2,3-Dimethyl-6((6-(pyrrolidin-1-yl)pyridin-2-yl)methoxy)imidazo[1,2-b]pyridazine According to the procedure described in example 9, the title compound was obtained as off-white solid.

MS: M=324.4 (M+H)+

Example 45

5,8-Dimethyl-2-(2-(6-(pyrrolidin-1-yl)pyridin-2-yl)ethyl)-[1,2,4]triazolo-[1,5-a]pyrazine

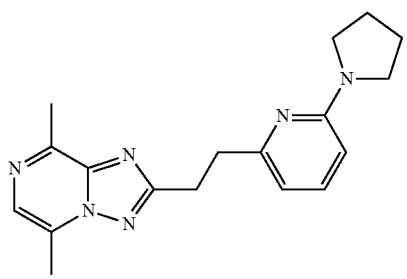 [SMILES: Cc1ncc(C)n2nc(CCc3cccc(N4CCCC4)n3)nc12]

The title compound was obtained from (E)-5,8-dimethyl-2-(2-(6-(pyrrolidin-1-yl)pyridin-2-yl)vinyl)[1,2,4]triazolo[1,5-a]pyrazine according to the procedure described in example 5. Yellow solid.

MS: M=323.1 (M+H)+

Example 46

5,7-Dimethyl-2-(2-(6-(pyrrolidin-1-yl)pyrazin-2-yl)ethyl)-[1,2,4]triazolo-[1,5-a]pyrimidine

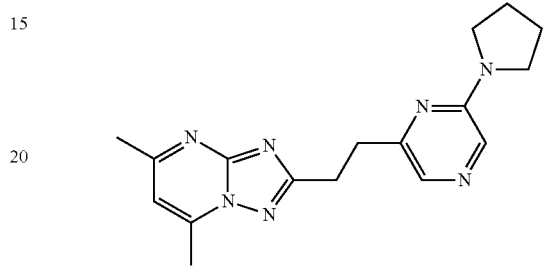

Step 1: 2-Bromo-6-(bromomethyl)pyrazine

To a solution of 2-bromo-6-methylpyrazine (3 g, 17.3 mmol) in carbon tetrachloride (30 ml) were added at r.t. under an argon atmosphere N-bromo succinimide (3.39 g, 19.1 mmol) and benzoyl peroxide (420 mg, 1.73 mmol). The mixture was stirred for 24 hr, while a 75 W lamp was shining on the orange reaction mixture). The mixture was filtered, washed with CCl₄ and concentrated. The residue was dissolved in EtOAc, washed with sat aq NaHCO₃, brine, dried over MgSO₄, filtered and concentrated. The crude product was purified by silica gel chromatography using a heptane/EtOAc gradient as eluent, providing the title compound (1.88 g, 43%) as brown solid.

Step 2: 2-[(E)-2-(6-Bromo-pyrazin-2-yl)-vinyl]-5,7-dimethyl-[1,2,4]triazolo[1,5-a]pyrimidine According to the procedures described in example 2, the title compound was obtained using 5,7-dimethyl-[1,2,4]triazolo[1,5-a]pyrimidine-2-carbaldehyde (CAS 55293-96-4) in the 2$^{nd}$ step (Wittig reaction). Pinkish solid.

MS: M=333.1 (M+H)+

Step 3: 5,7-Dimethyl-2-[(E)-2-(6-pyrrolidin-1-yl-pyrazin-2-yl)-vinyl]-[1,2,4]triazolo[1,5-a]pyrimidine According to the procedure described in example 25, step 2, the title compound was obtained from 2-[(E)-2-(6-bromo-pyrazin-2-yl)-vinyl]-5,7-dimethyl-[1,2,4]triazolo[1,5-a]pyrimidine and pyrolidine. Yellow solid.

MS: M=322.0 (M+H)+

Step 4: 5,7-Dimethyl-2-(2-(6-(pyrrolidin-1-yl)pyrazin-2-yl)ethyl)-[1,2,4]triazolo-[1,5-a]pyrimidine The title compound was obtained according to the procedure described in example 5. Light yellow solid.

MS: M=324.4 (M+H)+

Example 47

(E)-5,7-Dimethyl-2-(2-(6-(pyrrolidin-1-yl)pyridin-2-yl)vinyl)[1,2,4]triazolo[1,5-a]pyrimidine

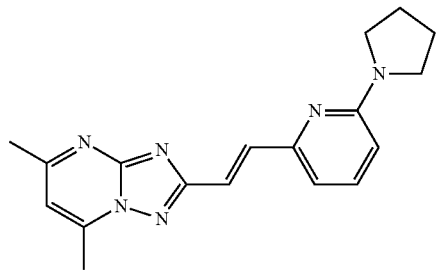 [SMILES: Cc1cc(C)n2nc(/C=C/c3cccc(N4CCCC4)n3)nc2n1]

Step 1: 2-(Bromomethyl)-6-(pyrrolidin-1-yl)pyridine

To a solution of (6-(pyrrolidin-1-yl)pyridin-2-yl)methanol (0.310 g, 1.74 mmol) in dichloromethane (10 ml) was added at r.t. under an argon atmosphere perbromomethane (1.15 g, 3.48 mmol) and triphenylphosphine (502 mg, 1.91 mmol). The mixture was stirred at 0° for 2 hrs.

The solvent was evaporated. The crude product was purified by silica gel chromatography using $CH_2Cl_2$ as eluent, to provide the title compound (210 mg, 90% purity, 45%) as solid.

MS: M=243.1 (M+H)+

Step 2: (E)-5,7-Dimethyl-2-(2-(6-(pyrrolidin-1-yl)pyridin-2-yl)vinyl)-[1,2,4]triazolo[1,5-a]pyrimidine According to the procedures described in example 2, the title compound was obtained reacting 5,7-dimethyl-[1,2,4]triazolo[1,5-a]pyrimidine-2-carbaldehyde (CAS 55293-96-4) and 2-(bromomethyl)-6-(pyrrolidin-1-yl)pyridine. Yellow solid.

MS: M=321.0 (M+H)+

Example 48

5,7-Dimethyl-2-[2-(6-pyrrolidin-1-yl-pyridin-2-yl)-ethyl]-[1,2,4]triazolo[1,5-a]pyrimidine

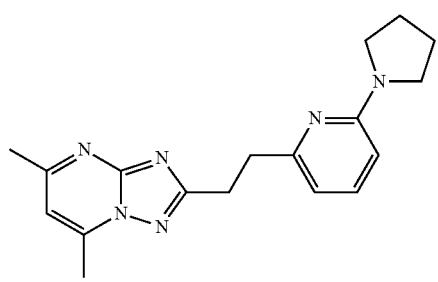 [SMILES: Cc1cc(C)n2nc(CCc3cccc(N4CCCC4)n3)nc2n1]

The title compound was obtained according to the procedure described in example 5. Yellow solid.

MS: M=323.0 (M+H)+

Example 49

2,3-Dmethyl-6-(2-(6-(pyrrolidin-1-yl)pyridin-2-yl)ethyl)imidazo[1,2-b]pyridazine

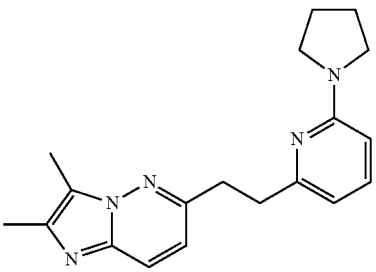

Step 1: 6-Iodopyridazin-3-amine

A suspension of 6-chloropyridazin-3-amine (7.35 g, 56.7 mmol) in hydroiodic acid 57% in water (102 g, 59.9 ml, 454 mmol) was heated to 100° C. under an argon atmosphere and stirring at that temperature was continued overnight. The dark reddish brown suspension was cooled to r.t. and EtOAc (5 ml) was added. The suspension was stirred vigorously for 5 min. The solid was then collected by filtration, washed with EtOAc and dried. The light yellow collected crystals were taken up in MeOH (120 ml), and sodium hydroxide (2.5 g, 62.4 mmol) was added to the suspension which was heated to reflux and stirred for 5 min, turning to an almost clear yellow solution. The mixture was cooled to r.t. and concentrated. The residue was triturated in 45 ml $H_2O$. The suspension was stirred at r.t. for 15 min. The product was collected by filtration, washed with $H_2O$ and dried to provide the title compound (10.9 g, 87%) as off-white solid.

MS: M=222.1 (M+H)+

Step 2: 6-Iodo-2,3-dimethylimidazo[1,2-b]pyridazine

A mixture of 6-iodopyridazin-3-amine (1.8 g, 8.14 mmol) and 3-bromobutan-2-one (1.65 g, 10.6 mmol) in ethanol (35.0 ml) under an argon atmosphere was heated to 85° C. overnight. The mixture was cooled to r.t. and concentrated to leave a brown foam. This was carefully taken up in 10% aq. $Na_2CO_3$ (15 ml). Then, EtOH (15 ml) was added. The resulting suspension was stirred at r.t. for 2 hrs. The solid was collected by filtration, washed with $H_2O$ and cyclohexane, and dried to give the title compound (823 mg, 37%) of the expected product as light brown powder.

MS: M=274.0 (M+H)+

Step 3: 2-(Pyrrolidin-1-yl)-6-((trimethylsilyl)ethynyl)pyridine

To a stirred solution of 2-bromo-6-(pyrrolidin-1-yl)pyridine (2 g, 8.81 mmol) and ethynyltrimethylsilane (1.08 g, 1.54 ml, 11.0 mmol) at r.t. in DMF (25 ml) under an argon atmosphere were added triethylamine (1.78 g, 2.44 ml, 17.6 mmol), copper(I) iodide (83.9 mg, 440 μmol) and bis (triphenylphosphine)palladium (II) dichloride (309 mg, 440 μmol). The mixture was evacuated and back-filled with argon before it was heated to 80° C. overnight. The mixture was cooled to r.t., diluted with EtOAc (50 ml) and washed with H₂O (25 ml). The aqueous phase was back extracted with EtOAc (50 ml). The combined organics were washed with H₂O (50 ml) and brine (50 ml), dried over MgSO₄, filtered and concentrated. The crude product was purified by silica gel chromatography using a n-heptane/EtOAc gradient as eluent, providing the title compound (1.56 g, 95% purity, 69%) as brown gum.

MS: M=245.4 (M+H)+

Step 4: 2-Ethynyl-6-(pyrrolidin-1-yl)pyridine

To a stirred, cooled (0° C.) solution of 2-(pyrrolidin-1-yl)-6-((trimethylsilyl)ethynyl)-pyridine (1.55 g, 6.34 mmol) in THF (30 ml) under an argon atmosphere was added dropwise tetrabutylammonium fluoride 1 M solution in THF (6.34 ml, 6.34 mmol). When the addition was complete, the ice bath was removed and stirring at r.t. was continued for 1 hr. The crude product was purified by silica gel chromatography using an n-heptane/EtOAc gradient as eluent, providing the title compound (910 mg, 83%) as brown solid.

MS: M=173.1 (M+H)+

Step 5: 2,3-Dimethyl-6-((6-(pyrrolidin-1-yl)pyridin-2-yl)ethynyl)imidazo[1,2-b]pyridazine To a stirred solution of 6-iodo-2,3-dimethylimidazo[1,2-b]pyridazine (200 mg, 732 μmol) and 2-ethynyl-6-(pyrrolidin-1-yl)pyridine (158 mg, 916 μmol) at r.t. in DMF (5 ml) under argon atmosphere were added triethylamine (148 mg, 203 μl, 1.46 mmol), copper(I) iodide (6.97 mg, 36.6 μmol) and bis(triphenylphosphine)palladium (II) chloride (25.7 mg, 36.6 μmol). The mixture was degassed and back-filled with argon before it was heated to 80° C. overnight. The mixture was cooled to r.t., diluted with EtOAc (15 ml) and washed with H₂O (15 ml). The aqueous phase was back extracted with EtOAc (15 ml). The combined organics were washed with H₂O (15 ml) and brine (15 ml), dried over MgSO₄, filtered and concentrated. The crude product was purified by silica gel chromatography using an n-heptane/EtOAc gradient as eluent, providing the title compound (174 mg, 95% purity, 70%) as brown solid.

MS: M=318.0 (M+H)+

Step 6: 2,3-Dimethyl-6-(2-(6-(pyrrolidin-1-yl)pyridin-2-yl)ethyl)imidazo[1,2-b]pyridazine To a stirred solution of 2,3-dimethyl-6-((6-(pyrrolidin-1-yl)pyridin-2-yl)ethynyl)-imidazo[1,2-b]pyridazine (168 mg, 498 μmol) at r.t. in methanol (4 ml) and CH₂Cl₂ (4.00 ml) under an argon atmosphere was added 10% Pd/C (17 mg). The black suspension was then stirred at r.t. under a hydrogen atmosphere for overnight. The catalyst was filtered off and washed with MeOH. The filtrate was concentrated. The crude product was purified by silica gel chromatography using a CH₂Cl₂/MeOH gradient as eluent, to provide the title compound (133 mg, 83%) as off-white solid.

MS: M=322.1 (M+H)+

Example 50

(E)-5,8-Dimethyl-2-(2-(6-(pyrrolidin-1-yl)pyrazin-2-yl)vinyl)[1,2,4]triazolo[1,5-a]pyrazine

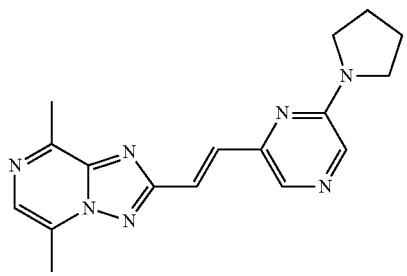 [SMILES: Cc1ncc(C)n2nc(/C=C/c3cncc(N4CCCC4)n3)nc12]

Step 1: 5,8-Dimethyl-[1,2,4]triazolo[1,5-a]pyrazin-2-yl)-methanol

To a solution of 2-chloromethyl-5,8-dimethyl-[1,2,4]triazolo[1,5-a]pyrazine (CAS 1201687-91-3, 5 g, 25.4 mmol) in DMSO (20 ml) were added sodium carbonate (3.234 g, 30.513 mmol) and water (300 ml). The resulting mixture was refluxed for 8 hrs. It was extracted with ethyl acetate (3×500 ml). The combined organics were washed with brine, dried over Na₂SO₄, filtered and concentrated. The crude product was purified by silica gel chromatography using 3% MeOH in CH₂Cl₂ as eluent to provide the title compound (3 g, 66%) as white solid. MS: M=179.0 (M+H)+

Step 2: 5,8-Dimethyl-[1,2,4]triazolo[1,5-a]pyrazine-2-carbaldehyde

To a solution of 5,8-dimethyl-[1,2,4]triazolo[1,5-a]pyrazin-2-yl)-methanol (4 g, 22.4 mmol) in dry ethyl acetate (200 ml) was added 2-iodoxybenzoic acid (18.857 g, 67.3 mmol). The reaction mixture was heated at reflux under argon atmosphere for 5 hrs. The reaction mixture was filtered through a bed of celite, the residue washed thoroughly with ethyl acetate. The filtrate was concentrated under reduced pressure. The crude product was purified by silica gel chromatography using CH₂Cl₂ as eluent to give the title compound (1.8 g, 46%) as white solid. GC-MS: 176 (m/z).

Step 3: (E)-5,8-Dimethyl-2-(2-(6-(pyrrolidin-1-yl)pyrazin-2-yl)vinyl)-[1,2,4]triazolo[1,5-a]pyrazine According to the procedures described in steps 1-3 of example 46, the title compound was obtained using 5,8-dimethyl-[1,2,4]triazolo[1,5-a]pyrazine-2-carbaldehyde and 2-bromo-6-(bromomethyl)pyrazine in the Wittig reaction. Yellow solid.

MS: M=322.3 (M+H)+

Example 51

5,8-Dimethyl-2-(2-(6-(pyrrolidin-1-yl)pyrazin-2-yl)ethyl)-[1,2,4]triazolo[1,5-a]pyrazine

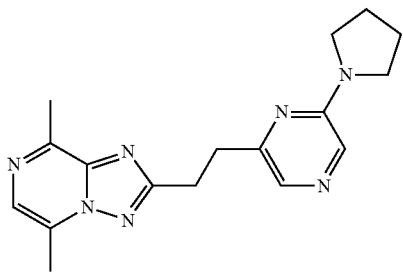 [SMILES: Cc1ncc(C)n2nc(CCc3cncc(N4CCCC4)n3)nc12]

The title compound was obtained from (E)-5,8-dimethyl-2-(2-(6-(pyrrolidin-1-yl)-pyrazin-2-yl)vinyl)[1,2,4]triazolo[1,5-a]pyrazine according to the procedure described in example 5. Light yellow solid.
MS: M=322.3 (M–H)–

Example 52

2-Ethyl-3-methyl-6-((6-(pyrrolidin-1-yl)pyridin-2-yl)methoxy)imidazo[1,2-b]pyridazine

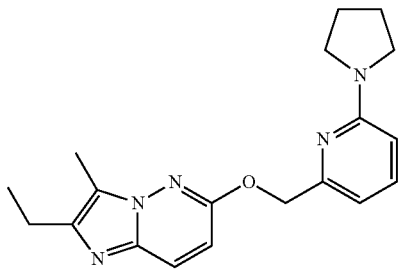 [SMILES: CCc1nc2ccc(OCc3cccc(N4CCCC4)n3)nn2c1C]

The title compound was obtained in analogy to the procedure described in example 44, using 2-bromo-pentan-3-one in the 1st step. Colorless solid.
MS: M=338.4 (M+H)+

Example 53

2,3-Dimethyl-5-((6-(pyrrolidin-1-yl)pyridin-2-yl)methoxy)pyrazolo[1,5-a]pyrimidine

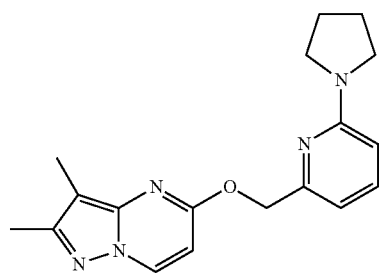 [SMILES: Cc1nn2ccc(OCc3cccc(N4CCCC4)n3)nc2c1C]

Step 1:
2,3-Dimethyl-pyrazolo[1,5-a]pyrimidine-5,7-diol

A sodium ethanolate solution (21% in EtOH; 35.1 g, 40.5 ml, 108 mmol) was added to ethanol (200 ml) at r.t. under an argon atmosphere. To this were added diethyl malonate (4.34 g, 4.11 ml, 27.1 mmol) and 4,5-dimethyl-1H-pyrazol-3-amine hydrochloride (4 g, 27.1 mmol). The mixture was heated to 85° C. overnight. The mixture was cooled to r.t. and treated with aq. 5 N HCl until pH~5 was reached. The mixture was concentrated to dryness, and the residue was used directly in the next step Step 2: 5,7-Dichloro-2,3-dimethyl-pyrazolo[1,5-a]pyrimidine A mixture of 2,3-dimethylpyrazolo[1,5-a]pyrimidine-5,7-diol (4.86 g, 27.1 mmol) and N,N-dimethylaniline (5.74 g, 6 ml, 47.3 mmol) in phosphoryl trichloride (98.7 g, 60 ml, 644 mmol) was heated to 115° C. under an argon atmosphere for 3 hrs. The brown suspension was cooled to r.t. and very carefully poured into 500 g of crushed ice. The resulting slurry was stirred at r.t. for 30 min and then extracted with $CH_2Cl_2$. The combined organics were washed with $H_2O$ and brine, dried over $MgSO_4$, filtered and concentrated to leave the crude product as a light brown sticky solid. The crude product was purified by silica gel chromatography using an n-heptane/EtOAc gradient as eluent, providing the title compound (2.63 g, 45%) as light brown solid.
MS: M=216.1 (M+H)+

Step 3:
5-Chloro-2,3-dimethyl-pyrazolo[1,5-a]pyrimidine

To a stirred suspension of 5,7-dichloro-2,3-dimethyl-pyrazolo[1,5-a]pyrimidine (2.61 g, 12.1 mmol) at r.t. in acetic acid (50 ml) under an argon atmosphere was added zinc dust (3.16 g, 48.3 mmol) in one portion. The reaction mixture was stirred at r.t. for 2 days. The white compact slurry was concentrated to dryness to leave a light brown solid which was suspended in $H_2O$ (60 ml). Then 15% aqueous $KHCO_3$ solution (50 ml) were added. The mixture was extracted with dichloromethane. The combined organics were washed with brine, dried over $MgSO_4$, filtered and concentrated. The crude product was purified by silica gel chromatography using an n-heptane/EtOAc gradient as eluent, providing the title compound (1.66 g, 76%) as yellow solid.
MS: M=182.1 (M+H)+

Step 4: 2,3-Dimethyl-5-((6-(pyrrolidin-1-yl)pyridin-2-yl)methoxy)pyrazolo[1,5-a]pyrimidine In analogy to the procedure described in example 9, the title compound was obtained by reaction 5-chloro-2,3-dimethyl-pyrazolo[1,5-a]pyrimidine and (6-(pyrrolidin-1-yl)pyridin-2-yl)methanol. Light yellow solid.
MS: M=324.4 (M+H)+

Example 54

2-Methyl-6-((6-(pyrrolidin-1-yl)pyridin-2-yl)methoxy)imidazo[1,2-b]pyridazine

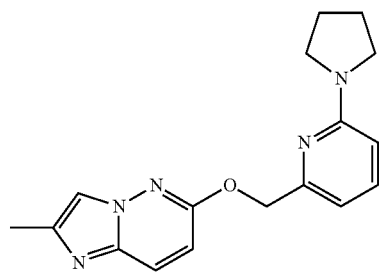 [SMILES: Cc1cn2nc(OCc3cccc(N4CCCC4)n3)ccc2n1]

The title compound was obtained in analogy to the procedure described in example 44, using 1-bromo-propan-2-one in the 1$^{st}$ step. Light yellow solid.
MS: M=310.3 (M+H)+

Example 55

2-Cyclopropyl-6-((6-(pyrrolidin-1-yl)pyridin-2-yl)methoxy)imidazo[1,2-b]pyridazine

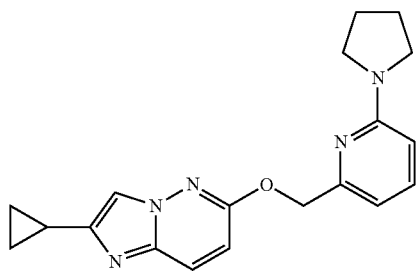 [SMILES: c1cc(COc2ccc3nc(C4CC4)cn3n2)nc(N2CCCC2)c1]

The title compound was obtained in analogy to the procedure described in example 44, using 2-bromo-1-cyclopropyl-ethanone in the 1st step. Light yellow solid.
MS: M=336.4 (M+H)+

Example 56

3-Methyl-6-((6-(pyrrolidin-1-yl)pyridin-2-yl)methoxy)imidazo[1,2-b]pyridazine-2-carboxamide

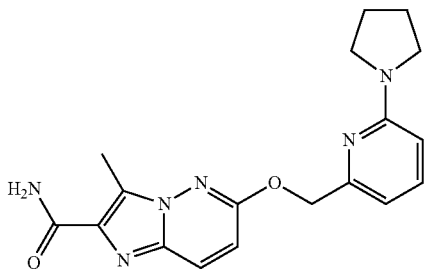 [SMILES: Cc1c(C(N)=O)nc2ccc(OCc3cccc(N4CCCC4)n3)nn12]

Step 1: 6-Chloro-3-methyl-imidazo[1,2-b]pyridazine-2-carboxylic acid methyl ester In analogy to the procedure described in step 1 of example 44, the title compound was prepared from 2-amino-5-chloropyridazine and 3-bromo-2-oxo-butyric acid methyl ester in 1,2-dimethoxyethane as solvent. Off-white solid.
MS: M=336.4 (M+H)+

Step 2: 6-Chloro-3-methyl-imidazo[1,2-b]pyridazine-2-carboxylic acid amide

To a solution of 6-chloro-3-methyl-imidazo[1,2-b]pyridazine-2-carboxylic acid methyl ester (1.5 g, 6.67 mmol) was dissolved in acetonitrile (20 ml) and treated with conc. aqueous ammonia solution (100 ml). The reaction mixture was stirred in a sealed tube at 100° C. for 10 hrs, then diluted with water and extracted with EtOAc. The combined organics were washed with water and brine, dried over Na$_2$SO$_4$ and concentrated. The crude product was purified by trituration with dichloromethane/hexanes to give the title compound (0.70 g, 50%) as off-white solid.

Step 3: 3-Methyl-6((6-(pyrrolidin-1-yl)pyridin-2-yl)methoxy)imidazo[1,2-b]pyridazine-2-carboxamide In analogy to the procedure described in example 9, the title compound was obtained as off-white solid.
MS: M=353.4 (M+H)+

Example 57

3-Methyl-N-((6-(pyrrolidin-1-yl)pyridin-2-yl)methyl)-2-(trifluoromethyl)imidazo[1,2-b]pyridazin-6-amine

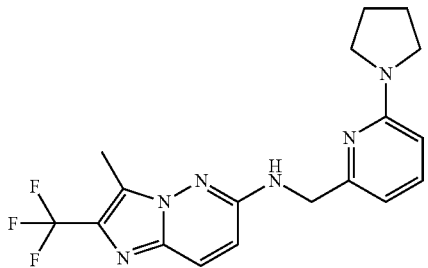 [SMILES: Cc1c(C(F)(F)F)nc2ccc(NCc3cccc(N4CCCC4)n3)nn12]

Step 1: (E)-6-(pyrrolidin-1-yl)picolinaldehyde oxime

To a solution of 6-(pyrrolidin-1-yl)picolinaldehyde (0.3 g, 1.7 mmol) in ethanol (10 ml) at r.t. under Ar were added hydroxylamine hydrochloride (142 mg, 2.04 mmol) and pyridine (161 mg, 164 µl, 2.04 mmol). The reaction mixture (yellow solution) was stirred by r.t. for 1 hr. The solvent was evaporated. The residue was diluted with H$_2$O and extracted with EtOAc. The organics were washed with H$_2$O, dried over MgSO$_4$, filtered and evaporated to provide a first crop of the title compound (95 mg). The aqueous phase was made basic with 1N NaOH 1N and was extracted with EtOAc. The organics were washed with H$_2$O, dried over MgSO$_4$, filtered and evaporated to provide a second crop of product (199 mg). The combined crops of crude product were purified by silica gel chromatography using a heptane/EtOAc gradient to provide the title compound (238 mg, 73%) as white solid.
MS: M=192.4 (M+H)+

Step 2: (6-(Pyrrolidin-1-yl)pyridin-2-yl)methanamine

To a suspension of (E)-6-(pyrrolidin-1-yl)picolinaldehyde oxime (230 mg, 1.2 mmol) in AcOH (8 ml) was added portionwise zinc powder (629 mg, 9.62 mmol). The mixture was stirred at r.t. for 3 hrs, then filtrated. The residue was washed with EtOH, the filtrate was concentrated. The crude product was purified by silica gel chromatography using a $CH_2Cl_2$/MeOH gradient to provide the title compound (168 mg, 79%) as yellow viscous oil.
MS: M=178.4 (M+H)+

Step 3: 3-Methyl-N-((6-(pyrrolidin-1-yl)pyridin-2-yl)methyl)-2-(trifluoromethyl)imidazo[1,2-b]pyridazin-6-amine A mixture of (6-(pyrrolidin-1-yl)pyridin-2-yl)methanamine (154 mg, 0.87 mmol), 6-chloro-3-methyl-2-(trifluoromethyl)imidazo[1,2-b]pyridazine (prepared in analogy to the procedure described in step 1 of example 44, using 3-bromo-1,1,1-trifluoro-butan-2-one in the 1st step; 205 mg, 0.87 mmol) and $K_2CO_3$ (265 mg, 1.9 mmol) in DMF (6 ml) was stirred at 80° C. overnight. The mixture was cooled to r.t., diluted with EtOAc and washed with $H_2O$. The aqueous phase was back extracted with EtOAc. The combined organics were washed with $H_2O$ and brine, dried over $MgSO_4$, filtered and evaporated. The crude product was purified by silica gel chromatography using a $CH_2Cl_2$/MeOH gradient to provide the title compound (19 mg, 6%) as yellow solid.
MS: M=377.3 (M+H)+

Example 58

2,3-Dimethyl-5-(2-(6-(pyrrolidin-1-yl)pyridin-2-yl)ethyl)pyrazolo[1,5-a]pyrimidine

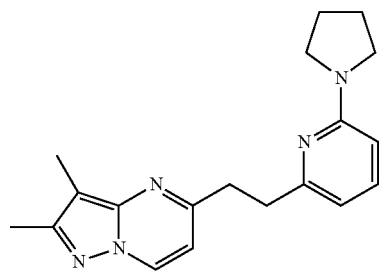 [SMILES: Cc1nn2ccc(CCc3cccc(N4CCCC4)n3)nc2c1C]

Step 1: 2,3-Dimethyl-5-vinylpyrazolo[1,5-a]pyrimidine

To a stirred solution 5-chloro-2,3-dimethylpyrazolo[1,5-a]pyrimidine (from example 53, step 3; 500 mg, 2.75 mmol) at r.t. in DMF (10 ml) under an argon atmosphere were added tributyl(vinyl)stannane (917 mg, 2.89 mmol) and Pd(PPh$_3$)$_4$ (159 mg, 138 µmol). The mixture was evacuated and back-filled with argon before it was heated to 120° C. Stirring at that temperature was continued overnight. The dark brown mixture was cooled to r.t., diluted with EtOAc and filtered. The filtrate washed with $H_2O$. The aqueous phase was extracted with EtOAc. The combined organics were washed with $H_2O$ and brine, dried over $MgSO_4$, filtered and concentrated. The crude product was purified by silica gel chromatography using a heptane/EtOAc gradient to provide the title compound (230 mg, 45%) as orange solid.
MS: M=174.2 (M+H)+

Step 2: (E)-2,3-Dimethyl-5-(2-(6-(pyrrolidin-1-yl)pyridin-2-yl)vinyl)pyrazolo[1,5-a]pyrimidine To a stirred solution of 2-bromo-6-(pyrrolidin-1-yl)pyridine (50 mg, 198 µmol) and 2,3-dimethyl-5-vinylpyrazolo[1,5-a]pyrimidine (51.5 mg, 297 µmol) at r.t. in DMF (3 ml) under an argon atmosphere were added triethylamine (100 mg, 137 µl, 991 µmol), tri-(o-tolyl)phosphine (12.1 mg, 39.6 µmol) and palladium(II) acetate (4.45 mg, 19.8 µmol). The mixture was degassed and flushed with argon before it was heated to 100° C. Stirring at that temperature was then continued overnight. The mixture was cooled to r.t., diluted with EtOAc and washed with H2O. The aqueous phase was back extracted with EtOAc. The combined organics were washed with H2O and brine, dried over MgSO4, filtered and concentrated. The crude product was purified by silica gel chromatography using a heptane/EtOAc gradient to provide the title compound (65 mg, 92%, 90% purity) as yellow solid.
MS: M=320.3 (M+H)+

Step 3: 2,3-Dimethyl-5-(2-(6-(pyrrolidin-1-yl)pyridin-2-yl)ethyl)pyrazolo[1,5-a]pyrimidine In analogy to the procedure described in example 5 the title compound was obtained as light yellow solid.
MS: M=322.2 (M+H)+

The invention claimed is:

1. A compound of formula (I)

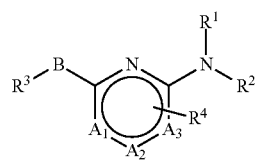

wherein $A_1$, $A_2$ and $A_3$ are C;

B is $C_1$-$C_4$-alkylene, $C_2$-$C_4$-alkenylene, —O—$C_1$-$C_4$alkyl or —NH—$C_1$-$C_4$alkyl;

$R^1$ and $R^2$ together with the nitrogen atom to which they are attached, form a azetidinyl, morpholinyl, pyrrolidinyl, piperidinyl or pyrazolidinyl ring which can be substituted by 1 to 3 substituents independently selected from the group consisting of halogen, $C_1$-$C_7$-alkyl, $C_1$-$C_7$-hydroxyalkyl, $C_1$-$C_7$ alkoxy, $C_1$-$C_7$-haloalkyl, hydroxyl and oxo;

$R^3$ is selected from the group consisting of:

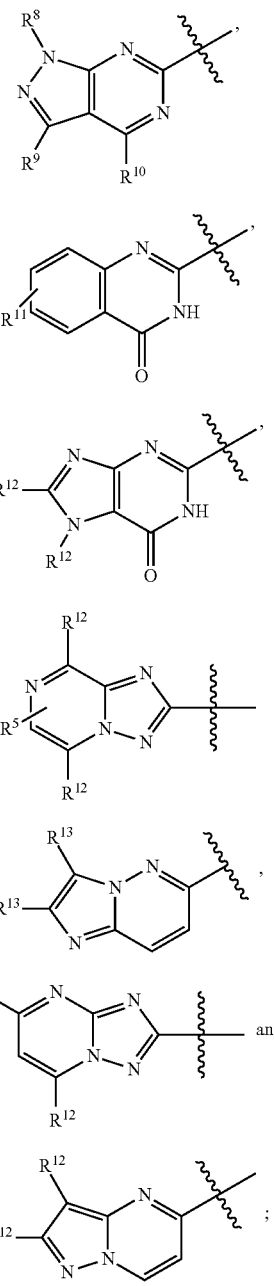

$R^8$, $R^9$ and $R^{10}$ are independently selected from hydrogen, $C_1$-$C_7$ alkyl or $NR^5R^6$;

$R^{11}$ is selected from hydrogen, halogen, $C_1$-$C_7$ alkyl or $C_1$-$C_7$ alkoxy;

$R^{12}$ is selected from hydrogen or $C_1$-$C_7$ alkyl;

$R^{13}$ is selected from hydrogen, $C_1$-$C_7$-alkyl optionally substituted by halogen, $C_3$-$C_8$ cycloalkyl, or —C(O)—NH$_2$;

$R^4$ is selected from hydrogen, $C_1$-$C_7$-alkyl or $C_3$-$C_8$-cycloalkyl;

$R^5$ and $R^6$ are independently selected from hydrogen or $C_1$-$C_7$-alkyl, or $R^5$ and $R^6$ together with the nitrogen atom to which they are attached, form a heterocycloalkyl which can be substituted by 1 to 3 substituents independently selected from the group consisting of halogen, $C_1$-$C_7$-alkyl, $C_1$-$C_7$-hydroxyalkyl, $C_1$-$C_7$ alkoxy, $C_1$-$C_7$-haloalkyl and oxo; or a pharmaceutically acceptable salts or pharmaceutically acceptable esters thereof.

2. The compound of claim 1, wherein B is $C_2$-$C_4$-alkylene, $C_2$-$C_4$-alkenylene, —O—$C_1$-alkyl or —NH—$C_1$-alkyl, preferably ethylene, ethenylene or —O—$C_1$-alkyl.

3. A compound selected from the group consisting of:
(E)-2-[2-(4-Methyl-6-pyrrolidin-1-yl-pyrimidin-2-yl)-vinyl]-quinoline,
(E)-4-(6-(2-(4-methoxy-3,5-dimethylpyridin-2-yl)vinyl)pyridin-2-yl)morpholine,
(E)-4-methoxy-3,5-dimethyl-2-(2-(6-(pyrrolidin-1-yl)pyridin-2-yl)vinyl)pyridine,
4-methoxy-3,5-dimethyl-2-(2-(6-(pyrrolidin-1-yl)pyridin-2-yl)ethyl)pyridine,
2-(2-(1-methyl-4-phenyl-1H-imidazol-2-yl)ethyl)-6-(pyrrolidin-1-yl)pyridine,
4-(6-(2-(1-methyl-4-phenyl-1H-imidazol-2-yl)ethyl)pyridin-2-yl)morpholine,
2,3,5-trimethyl-6-(2-(6-(pyrrolidin-1-yl)pyridin-2-yl)ethyl)pyrazine,
2-methyl-3-((6-(pyrrolidin-1-yl)pyridin-2-yl)methoxy)quinoxaline,
2-Methyl-3-[(E)-2-(6-pyrrolidin-1-yl-pyridin-2-yl)-vinyl]-quinoxaline,
2-Methyl-3-[2-(6-pyrrolidin-1-yl-pyridin-2-yl)-ethyl]-quinoxaline,
2-[2-(5-Methyl-2-phenyl-oxazol-4-yl)-ethyl]-6-pyrrolidin-1-yl-pyridine,
4-(6-chloro-2-((6-(pyrrolidin-1-yl)pyridin-2-yl)methoxy)quinazolin-4-yl)morpholine,
2-(2-(1-methyl-4-phenyl-1H-imidazol-2-yl)ethyl)-6-(pyrazolidin-1-yl)pyrazine,
2-methyl-3-((6-(piperidin-1-yl)pyridin-2-yl)methoxy)quinoxaline,
4-(2-((6-(pyrrolidin-1-yl)pyridin-2-yl)methoxy)quinazolin-4-yl)morpholine,
6-chloro-N,N-dimethyl-2-((6-(pyrrolidin-1-yl)pyridin-2-yl)methoxy)quinazolin-4-amine,
4-(1-methyl-6-((6-(pyrrolidin-1-yl)pyridin-2-yl)methoxy)-1H-pyrazolo[3,4-d]pyrimidin-4-yl)morpholine,
(E)-4-(6-chloro-2-(2-(6-(pyrrolidin-1-yl)pyridin-2-yl)vinyl)quinazolin-4-yl)morpholine,
4-(6-chloro-2-(2-(6-(pyrrolidin-1-yl)pyridin-2-yl)ethyl)quinazolin-4-yl)morpholine,
4-(2-(2-(6-(pyrrolidin-1-yl)pyridin-2-yl)ethyl)quinazolin-4-yl)morpholine,
6-chloro-2-((6-(pyrrolidin-1-yl)pyridin-2-yl)methoxy)-4-(tetrahydro-2H-pyran-4-yloxy)quinazoline,
4-[2-(2H-Pyrazol-3-yl)-6-(6-pyrrolidin-1-yl-pyridin-2-yl-methoxy)-pyrimidin-4-yl]-morpholine,
4-(2-(pyridin-3-yl)-6-((6-(pyrrolidin-1-yl)pyridin-2-yl)methoxy)pyrimidin-4-yl)morpholine,
(E)-(1-(6-(2-(6-chloro-4-(dimethylamino)quinazolin-2-yl)vinyl)pyridin-2-yl)pyrrolidin-3-yl)methanol,
5-chloro-2-(2-(6-(pyrrolidin-1-yl)pyridin-2-yl)ethyl)quinazolin-4(3H)-one,
6-chloro-5-methoxy-2-(2-(6-(pyrrolidin-1-yl)pyridin-2-yl)ethyl)quinazolin-4(3H)-one,
7,8-dimethyl-2-(2-(6-(pyrrolidin-1-yl)pyridin-2-yl)ethyl)-1H-purin-6(7H)-one,
6-chloro-2-(2-(6-(pyrrolidin-1-yl)pyridin-2-yl)ethyl)quinazolin-4(3H)-one, 2-(2-(6-(2,5-dimethylpyrrolidin-1-yl)pyridin-2-yl)ethyl)-N,N-dimethylquinazolin-4-amine,
1-(6-(2-(6-chloro-4-(dimethylamino)quinazolin-2-yl)ethyl)pyridin-2-yl)pyrrolidin-3-ol,
1-(6-(2-(4-(dimethylamino)quinazolin-2-yl)ethyl)pyridin-2-yl)pyrrolidin-3-ol,
(1-(6-(2-(6-chloro-4-(dimethylamino)quinazolin-2-yl)ethyl)pyridin-2-yl)pyrrolidin-3-yl)methanol,
(1-(6-(2-(4-(dimethylamino)quinazolin-2-yl)ethyl)pyridin-2-yl)pyrrolidin-3-yl)methanol,
(E)-6-chloro-N,N-dimethyl-2-(2-(6-(2-methylpyrrolidin-1-yl)pyridin-2-yl)vinyl)quinazolin-4-amine,
(E)-1-(6-(2-(6-chloro-4-(dimethylamino)quinazolin-2-yl)vinyl)pyridin-2-yl)pyrrolidin-2-one,
8-methyl-2-(2-(6-(pyrrolidin-1-yl)pyridin-2-yl)ethyl)quinazolin-4(3H)-one,
6-chloro-N,N-dimethyl-2-(2-(6-(2-methylpyrrolidin-1-yl)pyridin-2-yl)ethyl)quinazolin-4-amine,
(E)-5,8-dimethyl-2-(2-(6-(pyrrolidin-1-yl)pyridin-2-yl)vinyl)-[1,2,4]triazolo[1,5-a]pyrazine,
2,3-dimethyl-6-((6-(pyrrolidin-1-yl)pyridin-2-yl)methoxy)imidazo[1,2-b]pyridazine,
5,8-dimethyl-2-(2-(6-(pyrrolidin-1-yl)pyridin-2-yl)ethyl)-[1,2,4]triazolo[1,5-a]pyrazine,
5,7-dimethyl-2-(2-(6-(pyrrolidin-1-yl)pyrazin-2-yl)ethyl)-[1,2,4]triazolo[1,5-a]pyrimidine,
(E)-5,7-dimethyl-2-(2-(6-(pyrrolidin-1-yl)pyridin-2-yl)vinyl)-[1,2,4]triazolo[1,5-a]pyrimidine,
5,7-Dimethyl-2-[2-(6-pyrrolidin-1-yl-pyridin-2-yl)-ethyl]-[1,2,4]triazolo[1,5-a]pyrimidine,
2,3-dimethyl-6-(2-(6-(pyrrolidin-1-yl)pyridin-2-yl)ethyl)imidazo[1,2-b]pyridazine,
(E)-5,8-dimethyl-2-(2-(6-(pyrrolidin-1-yl)pyrazin-2-yl)vinyl)-[1,2,4]triazolo[1,5-a]pyrazine,
5,8-dimethyl-2-(2-(6-(pyrrolidin-1-yl)pyrazin-2-yl)ethyl)-[1,2,4]triazolo[1,5-a]pyrazine,
2-ethyl-3-methyl-6-((6-(pyrrolidin-1-yl)pyridin-2-yl)methoxy)imidazo[1,2-b]pyridazine,
2,3-dimethyl-5-((6-(pyrrolidin-1-yl)pyridin-2-yl)methoxy)pyrazolo[1,5-a]pyrimidine,
2-methyl-6-((6-(pyrrolidin-1-yl)pyridin-2-yl)methoxy)imidazo[1,2-b]pyridazine,
2-cyclopropyl-6-((6-(pyrrolidin-1-yl)pyridin-2-yl)methoxy)imidazo[1,2-b]pyridazine,
3-methyl-6-((6-(pyrrolidin-1-yl)pyridin-2-yl)methoxy)imidazo[1,2-b]pyridazine-2-carboxamide,
3-methyl-N-((6-(pyrrolidin-1-yl)pyridin-2-yl)methyl)-2-(trifluoromethyl)imidazo[1,2-b]pyridazin-6-amine, and,
2,3-dimethyl-5-(2-(6-(pyrrolidin-1-yl)pyridin-2-yl)ethyl)pyrazolo[1,5-a]pyrimidine; or
a pharmaceutically acceptable salt thereof.

4. The compound of claim 3 selected from the group consisting of:
2-methyl-3-((6-(pyrrolidin-1-yl)pyridin-2-yl)methoxy)quinoxaline,
4-(6-chloro-2-(2-(6-(pyrrolidin-1-yl)pyridin-2-yl)ethyl)quinazolin-4-yl)morpholine,
6-chloro-2-(2-(6-(pyrrolidin-1-yl)pyridin-2-yl)ethyl)quinazolin-4(3H)-one, and,
5,8-dimethyl-2-(2-(6-(pyrrolidin-1-yl)pyridin-2-yl)ethyl)-[1,2,4]triazolo[1,5-a]pyrazine; or
a pharmaceutically acceptable salt thereof.

5. A method for the treatment of psychotic disorders selected from the group consisting of schizophrenia, positive, negative and/or cognitive symptoms associated with schizophrenia, Parkinson's disease, restless leg syndrome, Alzheimer's disease, multi-infarct dementia, depression, psychosis, Huntington's disease and multiple sclerosis, comprising administering to a patient in need there of a pharmaceutically effective dose of a compound according to claim 1.

6. A pharmaceutical composition comprising a compound of claim 1, and at least one pharmaceutically acceptable excipient, carrier or diluent.

* * * * *